US012639124B2

(12) United States Patent
Drapkin et al.

(10) Patent No.: US 12,639,124 B2
(45) Date of Patent: *May 26, 2026

(54) MANAGING COMPUTER RESOURCES FOR CLINICAL APPLICATIONS

(71) Applicant: GE Precision Healthcare LLC, Waukesha, WI (US)

(72) Inventors: Evgeny Drapkin, Delafield, WI (US); Michael Braunstein, Mequon, WI (US); Fausto Espinal, Delafield, WI (US); David Minor, Tekoa (IL); Greg Ohme, Delafield, WI (US); Ben Dayan, Hadera (IL); David Chevalier, Menomonee Falls, WI (US); Manoj Unnikrishnan, Brookfield, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 147 days.

This patent is subject to a terminal disclaimer.

(21) Appl. No.: 18/429,269

(22) Filed: Jan. 31, 2024

(65) Prior Publication Data

US 2024/0168812 A1     May 23, 2024

Related U.S. Application Data

(63) Continuation of application No. 17/064,750, filed on Oct. 7, 2020, now Pat. No. 11,907,764.

(Continued)

(51) Int. Cl.
*G06F 9/50*          (2006.01)
*G06F 9/48*          (2006.01)
(Continued)

(52) U.S. Cl.
CPC ............ *G06F 9/5038* (2013.01); *G06F 9/485* (2013.01); *G06F 9/4881* (2013.01);
(Continued)

(58) Field of Classification Search
CPC ... G06F 9/45533–5083; G06F 2209/501–5014
See application file for complete search history.

(56) References Cited

U.S. PATENT DOCUMENTS

2006/0184943 A1     8/2006   Delmonego et al.
2008/0271039 A1    10/2008   Rolia et al.
(Continued)

FOREIGN PATENT DOCUMENTS

KR      10-2010-010351 A      9/2010

OTHER PUBLICATIONS

Practical Size based Scheduling for MapReduce Workloads Mario Pastorelli, Antonio Barbuzzi, Damiano Carra, Matteo Dell'Amico, Pietro Michiardi (Year: 2013).*
(Continued)

*Primary Examiner* — April Y Blair
*Assistant Examiner* — Paul V Mills
(74) *Attorney, Agent, or Firm* — Amin, Turocy & Watson, LLP

(57) ABSTRACT

Techniques regarding the management of computational resources based on clinical priority associated with one or more computing tasks are provided. For example, one or more embodiments described herein can regard a system comprising a memory that can store computer-executable components. The system can also comprise a processor, operably coupled to the memory, that executes the computer-executable components stored in the memory. The computer-executable components can include a prioritization component that can prioritize computer applications based on a clinical priority of tasks performed by the computer applications. The clinical priority can characterize a time sensitivity of the tasks. The computer-executable components can also include a resource pool component that can divide computational resources across a plurality of (Continued)

resource pools and can assign the computer applications to the plurality of resource pools based on the clinical priority.

20 Claims, 11 Drawing Sheets

Related U.S. Application Data

(60) Provisional application No. 63/027,565, filed on May 20, 2020.

(51) Int. Cl.

| | |
|---|---|
| *G06Q 10/0631* | (2023.01) |
| *G16H 40/20* | (2018.01) |
| *G16H 50/20* | (2018.01) |
| *G16H 70/20* | (2018.01) |

(52) U.S. Cl.
CPC ..... *G06F 9/5083* (2013.01); *G06Q 10/06312* (2013.01); *G06Q 10/06315* (2013.01); *G06Q 10/06316* (2013.01); *G16H 40/20* (2018.01); *G16H 50/20* (2018.01); *G16H 70/20* (2018.01)

(56) References Cited

U.S. PATENT DOCUMENTS

| | | | | |
|---|---|---|---|---|
| 2009/0235268 | A1 | 9/2009 | Seidman et al. | |
| 2010/0325277 | A1 | 12/2010 | Muthiah et al. | |
| 2011/0213886 | A1 | 9/2011 | Kelkar et al. | |
| 2011/0252430 | A1* | 10/2011 | Chapman | G06F 9/5011 |
| | | | | 718/107 |
| 2012/0096165 | A1 | 4/2012 | Madduri et al. | |
| 2012/0096167 | A1 | 4/2012 | Free et al. | |
| 2012/0284408 | A1 | 11/2012 | Dutta et al. | |
| 2013/0007272 | A1 | 1/2013 | Breitgand et al. | |
| 2013/0179574 | A1* | 7/2013 | Calder | G06F 9/45533 |
| | | | | 709/226 |
| 2013/0312006 | A1* | 11/2013 | Hardman | G06F 9/5027 |
| | | | | 718/105 |
| 2014/0022266 | A1 | 1/2014 | Metz et al. | |
| 2014/0173591 | A1 | 6/2014 | Lin et al. | |
| 2015/0066538 | A1 | 3/2015 | Dantsker et al. | |
| 2015/0070369 | A1 | 3/2015 | Frascati et al. | |
| 2015/0089501 | A1 | 3/2015 | Ganesan et al. | |
| 2015/0154056 | A1 | 6/2015 | Chen et al. | |
| 2015/0206408 | A1 | 7/2015 | Lalonde et al. | |
| 2015/0277981 | A1* | 10/2015 | Nalluri | G06F 9/5038 |
| | | | | 718/103 |
| 2016/0170801 | A1 | 6/2016 | Di Balsamo et al. | |
| 2016/0179572 | A1* | 6/2016 | Park | G06F 9/485 |
| | | | | 718/103 |
| 2016/0350919 | A1 | 12/2016 | Steigauf et al. | |
| 2017/0235677 | A1* | 8/2017 | Sakaniwa | G06F 12/0895 |
| | | | | 711/119 |
| 2017/0269964 | A1 | 9/2017 | Ashbaugh et al. | |
| 2020/0042359 | A1 | 2/2020 | Zhang et al. | |
| 2020/0159587 | A1* | 5/2020 | Li | G06F 9/4881 |
| 2020/0301740 | A1 | 9/2020 | Gabrielson et al. | |

OTHER PUBLICATIONS

Supervised Machine Learning Algorithms for Priority Task Classification in the Cloud Computing Environment Naoufal Er-raji, Faouzia Benabbou, Mirela Danubianu, Amal Zaouch (Year: 2018).*
Combining VM Preemption Schemes to Improve Vertical Memory Elasticity Scheduling in Clouds Jos'e Valencia, Cristina Boeres and Vinod E.F. Rebello (Year: 2018).*

Improving Preemptive Scheduling with Application-Transparent Checkpointing in Shared Clusters Jack Li, Calton Pu (Year: 2015).*
International Search Report and Written Opinion received for PCT Application Serial No. PCT/US2021/032771 dated Sep. 6, 2021, 10 pages.
Office Action mailed Jun. 27, 2022 for U.S. Appl. No. 17/064,750, 24 pages.
Prateek Sharma. "Transiency-driven Resource Management for Cloud Computing Platforms" University of Massachusetts Amherst Doctoral Dissertation, Chapters 1, 2, 6, and 7 (Year: 2018).
Lei Lu, Xiaoyun Zhu, Rean Griffith, Pradeep Padala. "Application-Driven Dynamic Vertical Scaling of Virtual Machines in Resource Pools" IEEE (Year: 2014) 9 pages.
Rongjun Xie, Ibrahim Khalil, Shahriar Badsha, Mohammed Atiquzzaman. "An intelligent healthcare system with data priority based on multi vital biosignals" Computer Methods and Programs in Biomedicine 185 (Year: 2019) 12 pages.
"Xiaoqiao Meng, Canturk Isci, Jeffrey Kephart, Li Zhang, Eric Bouillet, Dimitrios Pendarakis. ""Efficient Resource Provisioning in Compute Clouds via VM Multiplexing"" ICAC'10, Jun. 7-11, 2010, Washington, DC, USA. (Year: 2010), 10 pages."
Office Action mailed Feb. 1, 2023 for U.S. Appl. No. 17/064,750, 68 pages.
Rajeshwari Ganesan, Santonu Sarkar, Akshay Narayan. "Analysis of Saas Business Platform Workloads for Sizing and Collocation" 2012 IEEE Fifth International Conference on Cloud Computing, (Year: 2012) 8 pages.
Geetika Goel, Rajeshwari Ganesan, Santonu Sarkar, Kavish Kaup. "iCirrus WoP: Workload analysis for virtual machine placements" 2012 IEEE 18th International Conference on Parallel and Distributed Systems, (Year: 2012) 6 pages.
Jerry Rolia, Ludmila Cherkasova, Martin Arlitt, Artur Andrzejak. "A Capacity Management Service for Resource Pools" WOSP'05, Jul. 12-14, 2005, Palma de Mallorca, Spain (Year: 2005) 9 pages.
Ajay Gulati, Anne Holler, Minwen Ji, Ganesha Shanmuganathan. "VMware Distributed Resource Management: Design, Implementation, and Lessons Learned", [https://www.waldspurger.org/carl/papers/drs-vmtj-mar12.pdf] (Year: 2012) 20 pages.
Bhuvan Urgaonkar and Prashant Shenoy. "Sharc: Managing Resources in Shared Clusters" [https://lass.cs.umass.edu/papers/ps/TR01-08.pdf] (Year: 2001) 15 pages.
Bhuvan Urgaonkar, Prashant Shenoy and Timothy Roscoe. "Resource Overbooking and Application Profiling in Shared Hosting Platforms" Proceedings of the Fifth Symposium on Operating Systems Design and Implementation (OSDI '02), Dec. 9-11, 2002, Boston, Massachusetts, USA, (Year: 2002) 17 pages.
Sai Manohar Inabattini and Adarsh Jagadeeshwaran. "DRS Cluster Management With Reservation and Shares" [https://www.vmware.com/content/dam/digitalmarketing/vmware/en/pdf/techpaper/performance/drs-cluster-mgmt-perf.pdf] (Year: 2017) 16 pages.
Notice of Allowance mailed Oct. 12, 2023 for U.S. Appl. No. 17/064,750, 37 pages.
Jason Jong Kyu Park, Yongjun Park, Scott Mahlke. "Chimera Collaborative Preemption for Multitasking on a Shared GPU" ASPLOS '15, Mar. 14-18, 2015, Istanbul, Turkey. (Year: 2015) 14 pages.
Kyle Rupnow, Wenyin Fu, Katherine Compton. "Block, Drop or Roll(back): Alternative Preemption Methods for RH Multi-Tasking" 2009 17th IEEE Symposium on Field Programmable Custom Computing Machines (Year: 2009) 8 pages.
Dylan Machovec, Sudeep Pasricha, Anthony Maciejewski, Howard Jay Siegel, Gregory Koenig, Michael Wright, Marcia Hilton, Rajendra Rambharos, Thomas Naughton, and Neena Imam. "Preemptive Resource Management for Dynamically Arriving Tasks in an Oversubscribed Heterogeneous Computing System" 2017 IEEE International Parallel and Distributed Processing Symposium Workshops, (Year: 2017) 11 pages.

* cited by examiner

100

SERVER 102

MANAGEMENT COMPONENT 110

| COMMUNICATIONS COMPONENT 112 | MONITORING COMPONENT 114 | PRIORITIZATION COMPONENT 116 |

RESOURCE ALLOCATION COMPONENT 118

SYSTEM BUS 122

PROCESSOR 124

MEMORY 120

NETWORK(S) 104

EXECUTION REQUEST(S) 125

CLINICAL COMPUTER(S) 108

CLINICAL APPLICATIONS 126

COMPUTATIONAL RESOURCES 128

INPUT DEVICE(S) 106

Figure 2:
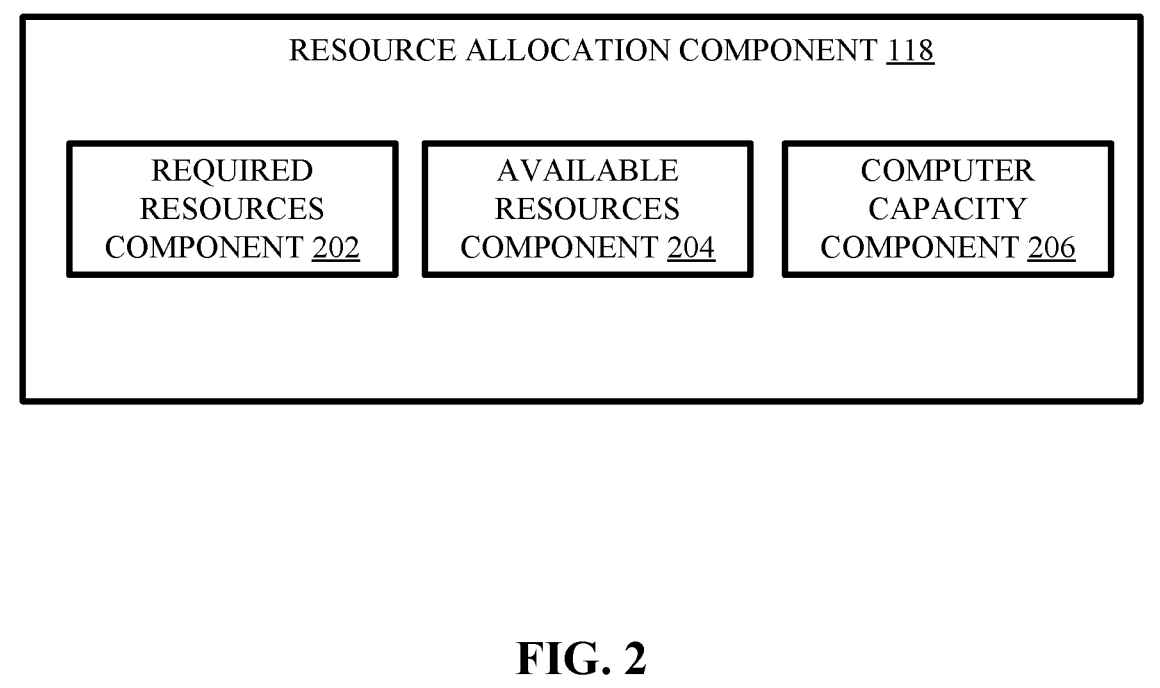

RESOURCE ALLOCATION COMPONENT 118

| REQUIRED RESOURCES COMPONENT 202 | AVAILABLE RESOURCES COMPONENT 204 | COMPUTER CAPACITY COMPONENT 206 |

SERVER 102

MANAGEMENT COMPONENT 110

| COMMUNICATIONS COMPONENT 112 | MONITORING COMPONENT 114 | PRIORITIZATION COMPONENT 116 |

| RESOURCE ALLOCATION COMPONENT 118 | RESOURCE POOL COMPONENT 302 |

SYSTEM BUS 122

PROCESSOR 124

MEMORY 120

APPLICATION LOG 304

NETWORK(S) 104

EXECUTION REQUEST(S) 125

CLINICAL COMPUTER(S) 108

CLINICAL APPLICATIONS 126

COMPUTATIONAL RESOURCES 128

INPUT DEVICE(S) 106

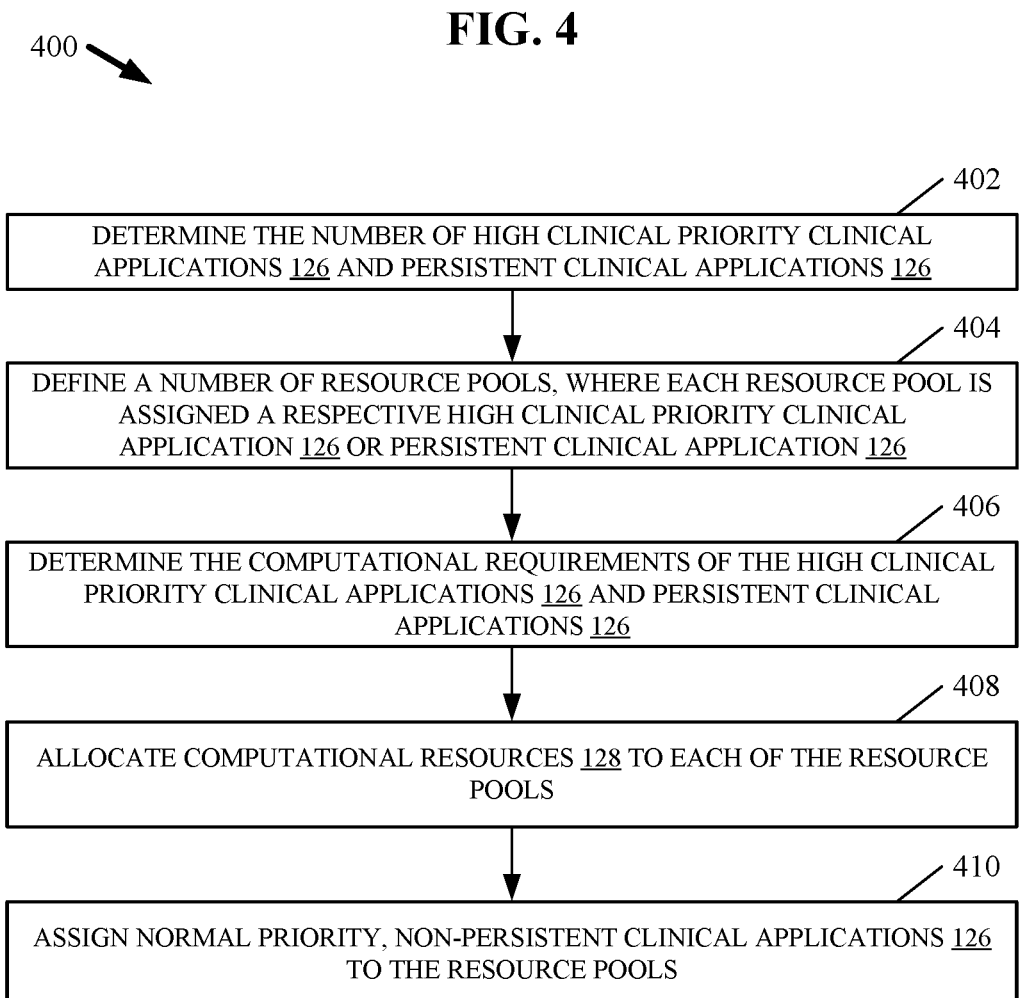

402
DETERMINE THE NUMBER OF HIGH CLINICAL PRIORITY CLINICAL APPLICATIONS 126 AND PERSISTENT CLINICAL APPLICATIONS 126

404
DEFINE A NUMBER OF RESOURCE POOLS, WHERE EACH RESOURCE POOL IS ASSIGNED A RESPECTIVE HIGH CLINICAL PRIORITY CLINICAL APPLICATION 126 OR PERSISTENT CLINICAL APPLICATION 126

406
DETERMINE THE COMPUTATIONAL REQUIREMENTS OF THE HIGH CLINICAL PRIORITY CLINICAL APPLICATIONS 126 AND PERSISTENT CLINICAL APPLICATIONS 126

408
ALLOCATE COMPUTATIONAL RESOURCES 128 TO EACH OF THE RESOURCE POOLS

410
ASSIGN NORMAL PRIORITY, NON-PERSISTENT CLINICAL APPLICATIONS 126 TO THE RESOURCE POOLS

SERVER 102

MANAGEMENT COMPONENT 110

| COMMUNICATIONS COMPONENT 112 | MONITORING COMPONENT 114 | PRIORITIZATION COMPONENT 116 |
|---|---|---|
| RESOURCE ALLOCATION COMPONENT 118 | RESOURCE POOL COMPONENT 302 | PRIORITY WEIGHT COMPONENT 502 |

PREEMPTION COMPONENT 504

SYSTEM BUS 122

PROCESSOR 124

MEMORY 120

APPLICATION LOG 304

NETWORK(S) 104

EXECUTION REQUEST(S) 125

CLINICAL COMPUTER(S) 108

CLINICAL APPLICATIONS 126

COMPUTATIONAL RESOURCES 128

INPUT DEVICE(S) 106

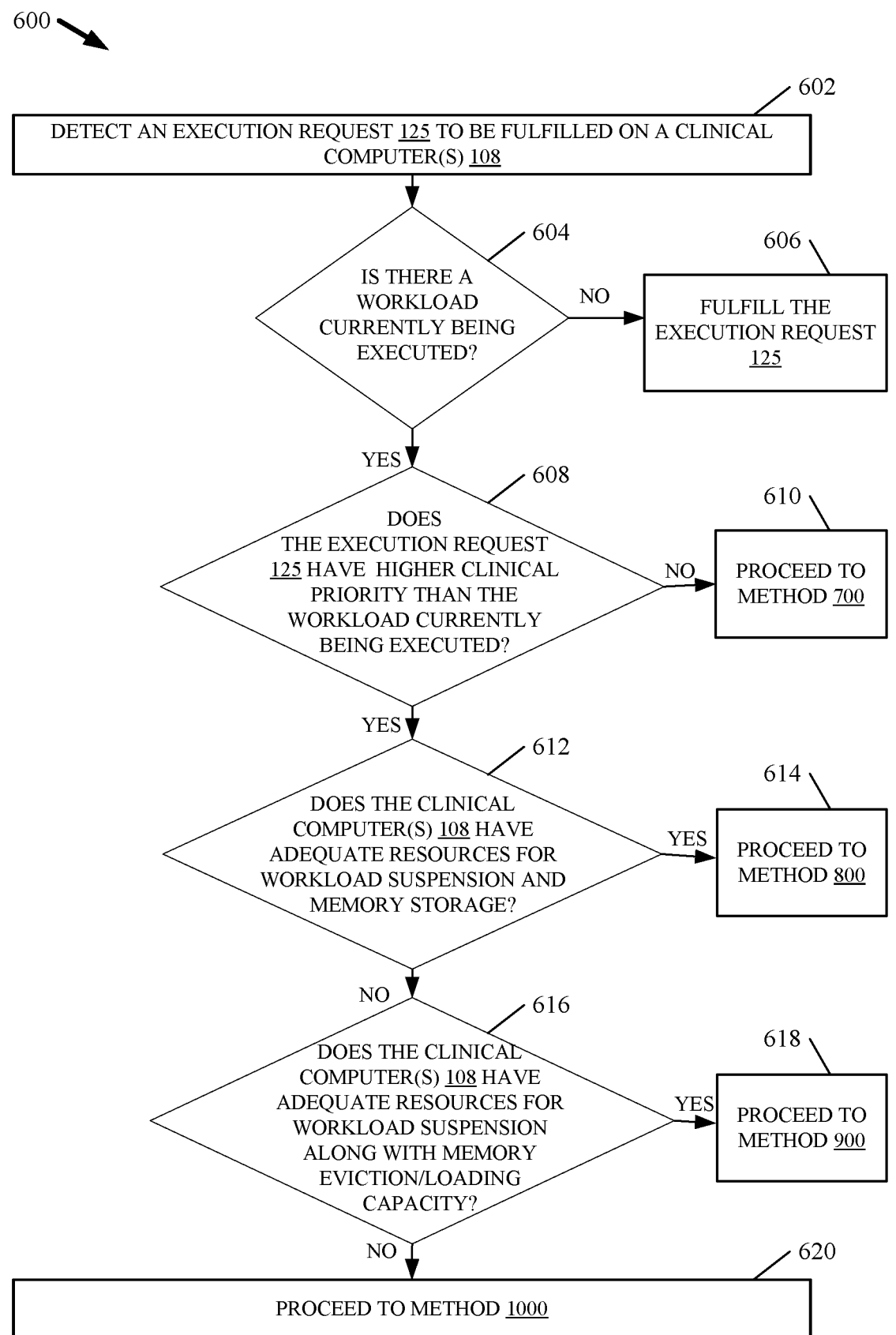

602

DETECT AN EXECUTION REQUEST 125 TO BE FULFILLED ON A CLINICAL COMPUTER(S) 108

604
IS THERE A WORKLOAD CURRENTLY BEING EXECUTED?

NO

606
FULFILL THE EXECUTION REQUEST 125

YES

608
DOES THE EXECUTION REQUEST 125 HAVE HIGHER CLINICAL PRIORITY THAN THE WORKLOAD CURRENTLY BEING EXECUTED?

NO

610
PROCEED TO METHOD 700

YES

612
DOES THE CLINICAL COMPUTER(S) 108 HAVE ADEQUATE RESOURCES FOR WORKLOAD SUSPENSION AND MEMORY STORAGE?

YES

614
PROCEED TO METHOD 800

NO

616
DOES THE CLINICAL COMPUTER(S) 108 HAVE ADEQUATE RESOURCES FOR WORKLOAD SUSPENSION ALONG WITH MEMORY EVICTION/LOADING CAPACITY?

YES

618
PROCEED TO METHOD 900

NO

620
PROCEED TO METHOD 1000

FREEZE EXECUTION OF THE WORKLOAD CURRENTLY BEING EXECUTED

1004

DUMP THE STATE OF THE FROZEN WORKLOAD

1006

TERMINATE EXECUTION OF THE FROZEN WORKLOAD

1008

FULFILL THE EXECUTION REQUEST 125

1010

RETRIEVE THE STATE OF THE TERMINATED WORKLOAD

1012

INITIATE EXECUTION OF THE TERMINATED WORKLOAD BASED ON THE RETRIEVED STATE

MANAGING COMPUTER RESOURCES FOR CLINICAL APPLICATIONS

CROSS-REFERENCE TO RELATED APPLICATIONS

This subject patent application claims priority to each of the following patent applications, and is a continuation of U.S. Non-Provisional patent application Ser. No. 17/064,750 (now U.S. Pat. No. 11,907,764), filed on Oct. 7, 2020, entitled "MANAGING COMPUTER RESOURCES FOR CLINICAL APPLICATIONS," which claims priority to U.S. Provisional Patent Application Ser. No. 63/027,565, filed on May 20, 2020, entitled "MANAGING COMPUTER RESOURCES FOR CLINICAL APPLICATIONS," the entireties of which patent applications are hereby incorporated by reference herein.

TECHNICAL FIELD

The subject disclosure relates to one or more computer-implemented methods and/or systems that can manage computer resources for various clinical applications, and more specifically, to managing the execution of one or more medical based computer program applications in response to an assessment of available computational resources.

BACKGROUND

In computerized systems used for medical purposes there is often a limited set of computation resources available for the various clinical applications employed by the system. For example, clinical applications related to medical scans, data processing, and/or image rendering may be employed on the same computer system. In most cases, clinical applications have different levels of clinical priority regarding the urgency of when respective applications should run, and/or whether data processing delays may have a negative impact on a patient well-being. For instance, data processing related to emergency cases (e.g., instances of stroke and/or critical trauma) can be associated with high clinical priority due to the time sensitive nature of one or more treatments dependent on the processing. In situations where multiple clinical applications share a limited set of computational resources, it is possible that the majority of resources could be occupied at time when emergency clinical applications need to be executed quickly.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses and/or computer program products that can regard the management of computational resources based on clinical priority are described.

According to an embodiment, a system is provided. The system can comprise a processor, operably coupled to the memory, that executes the computer-executable components stored in the memory. The computer-executable components can include a prioritization component that can prioritize computer applications based on a clinical priority of tasks performed by the computer applications. The clinical priority can characterize a time sensitivity of the tasks. The computer-executable components can also include a resource pool component that can divide computational resources across a plurality of resource pools and can assign the computer applications to the plurality of resource pools based on the clinical priority.

According to another embodiment, a computer-implemented method is provided. The computer-implemented method can comprise monitoring, by a system operably coupled to a processor, tasks associated with provisioning of computational resources. The computer-implemented method can further comprise identifying, by the system, a clinical priority of the tasks that characterizes a time sensitivity of the task. Also, the computer-implemented method can comprise expediting, by the system, fulfillment of one or more of the tasks by preempting completion of a computer workload based on the clinical priority.

According to another embodiment, a computer program product for managing computational resources is provided. The computer program product can comprise a computer readable storage medium having program instructions embodied therewith. The program instructions can be executable by a processor to cause the processor to monitor, by the processor, tasks associated with provisioning of computational resources. The program instructions can also cause the processor to identify, by the processor, a clinical priority of the tasks that characterizes a time sensitivity of the tasks. Further, the program instructions can cause the processor to expedite, by the processor, fulfillment of one or more of the tasks by preempting completion of a computer workload based on the clinical priority.

BRIEF DESCRIPTION OF THE DRAWINGS

FIG. 2 illustrates a block diagram of an example, non-limiting system that can comprise a resource allocation component that can determine status of computational resources in accordance with one or more embodiments described herein.

FIG. 4 illustrates a flow diagram of an example, non-limiting method that can be implemented to facilitate computational resource distribution in accordance with one or more embodiments described herein.

FIG. 5 illustrates a block diagram of an example, non-limiting system that can pre-empt execution of one or more clinical applications based on clinical priority in accordance with one or more embodiments described herein.

FIG. 6 illustrates a flow diagram of an example, non-limiting computer-implemented method that can facilitate managing execution of various clinical applications based on available computational resources and clinical priority in accordance with one or more embodiments described herein.

DETAILED DESCRIPTION

Figure 1:
FIG. 1 illustrates a block diagram of an example, non-limiting system that can manage execution of various clinical applications based on available computational resources and clinical priority in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Various embodiments of the present invention can be directed to computer processing systems, computer-implemented methods, apparatus and/or computer program products that facilitate the efficient, effective, and autonomous (e.g., without direct human guidance) management of the execution of clinical computer applications based on clinical priority regarding the well-being of a patient. For example, one or more embodiments described herein can regard analyzing clinical applications based on a clinical priority that regards an urgency associated with receiving the results of the clinical applications. For instance, clinical applications with high clinical priority can be applications that process data used in one or more time sensitive emergency medical treatments. Various embodiments described herein can redirect computational resources such that computer program applications and/or tasks having high clinical priority can be expeditiously executed over other pending applications and/or tasks having lower clinical priority. One or more embodiments described herein can employ one or more artificial intelligence and/or deep learning algorithms to enable persistent computer applications and/or tasks and high priority computer applications and/or tasks to run and meet latency requirements to facilitate positive patient outcomes. Thereby, the full computational potential of a computer system employed in a medical environment can be leveraged to execute high clinical priority applications and/or tasks in an expeditious manner.

The computer processing systems, computer-implemented methods, apparatus and/or computer program products employ hardware and/or software to solve problems that are highly technical in nature (e.g., the allocation of computational resources across a computer system employed for medical purposes), that are not abstract and cannot be performed as a set of mental acts by a human. For example, an individual, or a plurality of individuals, cannot readily and/or efficiently ascertain the computational needs of a pending clinical application in relation to the computational resources of a computer system in determining an efficient means for directing the resources to clinical applications based on clinical priority.

Also, one or more embodiments described herein can constitute a technical improvement over conventional clinical application executions by defining a computer resource scheme for distributing computer resources based on clinical priority. Additionally, various embodiments described herein can demonstrate a technical improvement over conventional clinical application executions by reducing latency for computer applications executing high clinical priority tasks and/or applications executing persistent tasks that are responsive to medical data streaming from a medical device.

Further, one or more embodiments described herein can have a practical application by managing a limited set of computational resources to execute a plurality of medical applications while minimizing latency experienced by time sensitive applications and/or tasks. For instance, various embodiments described herein can divide the computational resources into pools, with each medical application assigned to a respective pool. The resource pools can be defined based on the computational resources available and the demands of the medical applications. Thereby, multiple applications with high clinical priority can run on separate pools of computation resources without delaying each other's execution. One or more embodiments described herein can further control the order of execution employed by each resource pool. Thereby, the one or more embodiments can preempt execution of one or more applications to expedite execution of another application associated with high clinical priority.

As used herein, the term "clinical priority" can refer to a level of priority associated with the execution of a computer application and/or task based on time sensitivity of a medical treatment and/or diagnosis. For example, computer applications and/or tasks with high clinical priority can be ones in which the resulting data is utilized in the treatment and/or diagnosis of one or more emergency medical scenarios (e.g., scenarios involving a stroke, heat attack and/or severe trauma). Computer applications and/or tasks employed to facilitate the treatment and/or diagnosis of less urgent medical implications can be associated with a lower clinical priority. Thereby, clinical priority can describe the time sensitivity associated with the execution of a computer application and/or task, wherein the clinical priority increases as the execution becomes more time sensitive. For instance, delays in the execution of a computer application and/or task having low clinical priority will have a smaller negative impact on the effectiveness of a medical treatment and/or diagnosis than the negative impact caused by delays in the execution of a computer application and/or task having high clinical priority.

FIG. 1 illustrates a block diagram of an example, non-limiting system 100 that can manage the execution of various computer applications based on clinical priority. Repetitive description of like elements employed in other embodiments described herein is omitted for sake of brevity. Aspects of systems (e.g., system 100 and the like), apparatuses or processes in various embodiments of the present invention can constitute one or more machine-executable components embodied within one or more machines (e.g., embodied in one or more computer readable mediums (or media) associated with one or more machines). Such components, when executed by the one or more machines (e.g., computers, computing devices, virtual machines, etc.) can cause the machines to perform the operations described.

As shown in FIG. 1, the system 100 can comprise one or more servers 102, one or more networks 104, input devices 106, and/or clinical computers 108. The server 102 can comprise management component 110. The management component 110 can further comprise communications component 112, monitoring component 114, prioritization component 116, and/or resource allocation component 118. Also, the server 102 can comprise or otherwise be associated with at least one memory 120. The server 102 can further comprise a system bus 122 that can couple to various components such as, but not limited to, the management component 110 and associated components, memory 120 and/or a processor 124. While a server 102 is illustrated in FIG. 1, in other embodiments, multiple devices of various types can be associated with or comprise the features shown in FIG. 1. Further, the server 102 can communicate with one or more cloud computing environments.

The one or more networks 104 can comprise wired and wireless networks, including, but not limited to, a cellular network, a wide area network ("WAN") (e.g., the Internet) or a local area network ("LAN"). For example, the server 102 can communicate with the one or more input devices 106 and/or clinical computers 108 (and vice versa) using virtually any desired wired or wireless technology including for example, but not limited to: cellular, WAN, wireless fidelity ("Wi-Fi"), Wi-Max, WLAN, Bluetooth technology, a combination thereof, and/or the like. Further, although in the embodiment shown the management component 110 can be provided on the one or more servers 102, it should be appreciated that the architecture of system 100 is not so limited. For example, the management component 110, or one or more components of management component 110, can be located at another computer device, such as another server device, a client device, etc.

The one or more input devices 106 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. In various embodiments, the one or more input devices 106 can be employed to enter one or more execution requests 125 into the system 100, thereby sharing (e.g., via a direct connection and/or via the one or more networks 104) said data with the server 102 and/or the one or more clinical computers 108. For example, the one or more input devices 106 can send data to the communications component 112 (e.g., via a direct connection and/or via the one or more networks 104). Additionally, the one or more input devices 106 can comprise one or more displays that can present one or more outputs generated by the system 100 to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

In various embodiments, the one or more input devices 106 and/or the one or more networks 104 can be employed to input one or more settings and/or commands into the system 100. For example, in the various embodiments described herein, the one or more input devices 106 can be employed to operate and/or manipulate the server 102 and/or associate components. Additionally, the one or more input devices 106 can be employed to display one or more outputs (e.g., displays, data, visualizations, and/or the like) generated by the server 102 and/or associate components. Further, in one or more embodiments, the one or more input devices 106 can be comprised within, and/or operably coupled to, a cloud computing environment. In one or more embodiments, the one or more input devices 106 can be employed to generate and/or share one or more execution requests 125 that can delineate one or more tasks to be performed by the clinical computers 108. For instances, the execution requests 125 can direct the one or more clinical computers 108 to collect and/or processes desirable data pertaining to a medical treatment, observation, and/or diagnosis.

The one or more clinical computers 108 can be one or more computer systems employed to fulfill the execution requests 125 and/or facilitate one or more medical treatments, observations, and/or diagnoses. For example, the one or more clinical computers 108 can perform various medical imaging procedures, such as, but not limited to: magnetic resonance imaging ("MRI"), ultrasounds, computed tomography ("CT") scans, X-rays, women's health procedures (e.g., mammography), patient vital signal monitoring (e.g., monitoring blood pressure and/or respiratory signals), electrocardiograms ("EKGs"), live video streams from intensive care units, a combination thereof, and/or the like. In another example, the one or more clinical computers 108 can perform various data processing procedures such as, but not limited to: image adjustments (e.g., noise and/or motion corrections), data transfers, electronic health record management, medical diagnosis determinations, medical database analyses (e.g., including a patient's medical history, medications, and/or procedures), electronic prescribing, appointment scheduling, medical equipment management, hospital management, medical billing, a combination thereof, and/or the like. In various embodiments, the one or more clinical computers 108 can be employed by medical professionals to collect data regarding a patient's condition (e.g., perform tests and/or scans) and/or manage medical equipment (e.g., control one or more medical instrumentation).

Additionally, the one or more clinical computers 108 can include one or more clinical applications 126. The one or more clinical applications 126 can be one or more computer programs that can be executed by the one or more clinical computers 108 to perform the various tasks delineated by the execution requests 125. For example, a stroke assessment clinical application 126 can be a computer program that instructs the one or more clinical computers 108 to operate one or more scanners and/or sensors in a defined sequence so as to collect a prescribed amount and/or type of data regarding the condition of a patient. In another example, a CT scan clinical application 126 can be a computer program that instructs the one or more clinical computers 108 to perform a CT scan in accordance with one or more defined parameters. In various embodiments, the one or more execution requests 125 can include one or more settings (e.g., defined by a medical professional via the one or more input devices 106) that can guide the performance of the one or more clinical applications 126 in completing the desired task.

In one or more embodiments, each function performed by the one or more clinical computers 108 can be facilitated by one or more associate clinical applications 126. Additionally, the one or more clinical applications 126 can be employed via the one or more clinical computers 108 to fulfill the execution requests 125 entered into the system 100 by the one or more input devices 106. For example, one or more users of the system 100 (e.g., medical professionals) can employ the one or more input devices 106 to enter one or more execution requests 125 to be fulfilled by the one or more clinical computers 108 and/or facilitated by the one or more clinical applications 126. The execution requests 125 can be shared with the one or more servers 102 and/or clinical computers 108 via the one or more networks 104 and/or direct electrical connections.

Further, the one or more execution requests 125 can be characterized by a clinical priority. In one or more embodiments, respective execution requests 125 can be characterized by an inherit clinical priority. For example, execution requests 125 can be characterized by clinical priority based on type. For instance, one or more databases (e.g., stored in the one or more memories 120) can list the types of execution requests 125 that can be submitted by the input devices 106 and/or fulfilled by the clinical computers 108 and the clinical priority associated with each type.

In some embodiments, the clinical priority of an execution request 125 can vary based on the context of its generation. For example, an execution request 125 for a medical scan may have a low clinical priority when generated to facilitate a routine check-up, but a high clinical priority when generated to observe the condition of trauma patient. The context of the execution requests 125 can be defined in the development of the execution requests 125 by the one or more input devices 106. For instance, a execution request 125 can delineate an intended purpose for the results of the clinical application 126, and/or the need for the clinical application 126; where the clinical priority can be defined based on the intended purpose and/or need. In some embodiments, the clinical priority associated with a execution request 125 can be predefined by the one or more input devices 106. For instance, a medical professional can employ the one or more input devices 106 to enter into the system 100 an execution request 125 and define the clinical priority within the execution request 125.

In various embodiments, the communications component 112 can receive data from the one or more input devices 106 and/or clinical computers 108 via the one or more networks 104 and/or direct electrical connections. Further, the communications component 112 can share the received data with one or more associate components of the management component 110. For example, the communications component 112 can receive one or more execution requests 125 generated and/or entered by the one or more input devices 106. In another example, the communications component 112 can receive data from the one or more clinical computers 108 regarding, for instance: the computational resources of the one or more clinical computers 108, clinical applications 126 being executed by the clinical computers 108, clinical applications 126 in queue for execution by the clinical computers 108, a combination thereof, and/or the like.

In one or more embodiments, the monitoring component 114 can monitor tasks associated with provisioning of computational resources 128 of the one or more clinical computers 108. For example, the monitoring component 114 can monitor the one or more clinical computers 108 to determine when one or more clinical applications 126 are being executed. In another example, the monitoring component 114 can monitor the one or more input devices 106 to detect the generation and/or submittal of one or more execution requests 125.

In one or more embodiments, the prioritization component 116 can assign one or more clinical priorities to the execution requests 125 generated by the one or more input devices 106. For example, the prioritization component 116 can analyze an execution request 125 to determine an associate clinical priority based on its type. For instance, the prioritization component 116 can identify the type of the execution request 125 based on an included identifier and/or the respective clinical applications 126 that would be employed to fulfill the execution request 125. Further, the prioritization component 116 can reference a clinical priority database (e.g., stored in the memory 120) that delineates respective clinical priorities for each type of possible execution request 125.

In another example, the prioritization component 116 can analyze the execution requests 125 to determine an associated clinical priority based on a context described in the execution requests 125. For instance, the execution requests 125 can describe the intended purpose associated with the generation of the execution requests 125 (e.g., can describe that the execution requests 125 were generated with regards to a life threatening injury), and the prioritization component 116 can assign a clinical priority to the execution requests 125 based on the intended purpose. In another instance, the execution requests 125 can describe a time sensitivity and/or urgency associated with the fulfillment (e.g., the execution requests 125 can be marked urgent), and the prioritization component 116 can assign a clinical priority to the execution requests 125 based on the time sensitivity and/or urgency. In a further instance, the execution requests 125 can describe a source of the request (e.g., can describe a unit of the medical facility, such as the intensive care unit, and/or a medical professional submitting the execution requests 125), and the prioritization component 116 can assign a clinical priority to the execution requests 125 based on the source.

In various embodiments, the prioritization component 116 can employ one or more artificial intelligence technologies to learn from past clinical priority assignments and/or determine the clinical priority to be assigned to a new execution request 125. For example, the prioritization component 116 can employ one or more machine learning models to learn from past execution requests 125 in which the clinical priority was preassigned (e.g., by the medical professional employing the input devices 106 to generate the request), and apply the learned lessons to assign a clinical priority to a execution request 125 received without a preassigned clinical priority. For instance, the prioritization component 116 can assign a clinical priority to a execution request 125 based on clinical priorities associated with past execution requests 125 having the same or similar parameters (e.g., regarding the same type of clinical application 126, intended use, and/or generation source).

In one or more embodiments, the resource allocation component 118 can determine the computer resource allocation amongst the one or more clinical computers 108. For example, the one or more clinical computers 108 can have a limited amount of computational resources 128, wherein the resource allocation component 118 can determine the computational capabilities of the clinical computers 108. Example, computational resources 128 of the one or more clinical computers 108 can include, but are not limited to: central processing unit ("CPU") cores, computer memory, accelerator processing cores (e.g., graphics processing unit ("GPU") cores), accelerator memory, a combination thereof, and/or the like. The one or more clinical computers 108 can utilize the computational resources 128 to execute the one or more clinical applications 126. Thus, the amount of computational resources 128 available to fulfill a execution request 125 can depend on the capabilities of the clinical computers 108 and/or the amount of computational resources 128 currently being employed to execute clinical applications 126.

FIG. 2 illustrates a diagram of the example, non-limiting resource allocation component 118 further comprising required resources component 202, available resources component 204, and/or computer capacity component 206 in accordance with one or more embodiments described herein. Repetitive description of like elements employed in other embodiments described herein is omitted for sake of brevity.

In various embodiments, the required resources component 202 can determine the computational resources 128 required to fulfill one or more execution requests 125. For example, the required resources component 202 can determine how many CPU and/or accelerator cores will be required to fulfill the execution requests 125, and/or the amount of computer and/or accelerator memory required to fulfill the execution requests 125. In one or more embodiments, the computational resources 128 required to fulfill an execution request 125 can depend on the type of execution request 125 to be fulfilled and/or the type of tasks directed by the execution request 125.

In one or more embodiments, the available resources component 204 can track the availability of the clinical computers' 108 computational resources 128. For example, the available resources component 204 can track the status of each computational resource 128 of the clinical computers 108. As the clinical computers 108 execute clinical applications 126, and thereby engage the computational resources 128, the available resources component 204 can update the status of the computational resources 128. Thus, in various embodiments the available resources component 204 can identify the computational resources 128 being engaged by the clinical computers 108 and the computational resources 128 free for engagement at a given moment.

In one or more embodiments, the computer capacity component 206 can determine the computational capacity of the clinical computers 108 based on the computational resources 128 of the clinical computers 108. For example, the computer capacity component 206 can determine if one or more computing features are enabled by the computational resources 128. For instance, the computer capacity component 206 can identify one or more memory units of the computational resources 128 to determine the storage capacity of the one or more clinical computers 108. In another instance, the computer capacity component 206 can identify the CPUs and/or accelerators included in the computational resources 128 to determine the data processing capacity of the one or more clinical computers 108. In a further instance, the computer capacity component 206 can analyze the computational resources 128 to determine whether the one or more clinical computers 108 can, for example: employ one or more memory swap procedures, utilize virtual memory, evict and/or load memory data, a combination thereof, and/or the like.

Figure 3:
FIG. 3 illustrates a block diagram of an example, non-limiting system that can comprise resource pool component 302 that can divide computational resources amongst a plurality of resource pools in accordance with one or more embodiments described herein.

FIG. 3 illustrates a diagram of the example, non-limiting management component 110 further comprising resource pool component 302 in accordance with one or more embodiments described herein. Repetitive description of like elements employed in other embodiments described herein is omitted for sake of brevity. In various embodiments, the resource pool component 302 can divide the computational resources 128 of the clinical computers 108 into defined resource pools assigned to respective clinical applications 126.

In one or more embodiments, the resource pool component 302 can divide the computational resources 128 (e.g., CPU cores, CPU memory, GPUs, other accelerators, persistent storage, network storage, and/or the like) into a plurality of resource pools. Each resource pool can be a collective of computational resources 128 that can be employed to execute a clinical application 126. The number of resource pools defined by the resource pool component 302 can depend on the number of clinical applications 126 associated with a high clinical priority and/or the number of persistent clinical applications 126. In accordance with various embodiments described herein, the prioritization component 116 can identify the level of clinical priority associated with each of the plurality of clinical applications 126 that can be executed by the one or more clinical computers 108. Thereby, the resource pool component 302 can identify the number of clinical applications 126 with high clinical priority. For example, where clinical priority is delineated by the prioritization component 116 via a priority value, the resource pool component 302 can define a resource pool for each clinical application 126 characterized by a priority value that is greater than or equal to a defined threshold. In another example, where clinical priority is delineated by the prioritization component 116 via a priority identifier (e.g., a clinical application 126 can be labeled "high priority" or "normal priority"), the resource pool component 302 can define a resource pool for each clinical application 126 characterized by a high clinical priority identifier (e.g., for each clinical application 126 labeled "high priority"). In one or more embodiments, the resource pool component 302 can define a respective resource pool for each high clinical priority clinical application 126.

Additionally, the resource pool component 302 can define a respective resource pool for each persistent clinical application 126. In various embodiments, persistent clinical applications 126 can be clinical applications 126 that require low latency responses to execution requests 125 and/or processing of medical device data. For instance, persistent clinical applications 126 can be clinical applications 126 in which the performance of the clinical application 126 can be dependent on the latency between the clinical application 126 and one or more inputs (e.g., entered via the one or more input devices 106 by a medical practitioner and/or medical device). Examples of persistent clinical applications 126 can include, but are not limited to: high acuity patient monitoring, clinician image manipulation analysis, clinical and medical devices (e.g., medical services), data collection and aggregation, volume rendering interactive image volume manipulation, a combination thereof, and/or the like.

By defining the total number of resource pools as a function of the high clinical priority clinical applications 126 and persistent clinical applications 126, the resource pool component 302 can ensure that the high clinical priority clinical applications 126 and persistent clinical applications 126 have access to computational resources 128 on-demand and with low latency of activation. Further, the resource pool component 302 can define the resource pools such that computational resources 128 of each resource pool do not overlap. For example, where the resource pool component 302 defines three resource pools "A", "B", and "C"; the computational resources 128 allocated to resource pool A can be distinct from those computational resources 128 allocated to resource pools B and C. Likewise, the computational resources 128 allocated to resource pool B can be distinct from those computational resources 128 allocated to resource pools A and C. Further, the computational resources 128 allocated to resource pool C can be distinct from those computational resources 128 allocated to resource pools A and B. Thereby, each resource pool defined by the resource pool component 302 can be a distinct, non-overlapping subset allocation of the total computational resources 128 available to the one or more clinical computers 108.

In various embodiments, resource pool component 302 can further assign the execution of one or more clinical applications 126 to the resource pools. For example, each high clinical priority clinical application 126 and/or persistent clinical applications 126 can be assigned a respective resource pool, where execution of the clinical application 126 is fulfilled by employing the subset of computational resources 128 allocated to the resource pool. For instance, where the clinical applications 126 include two high clinical priority applications 126 and one persistent clinical application 126, the resource pool component 302 can define at least three resource pools (e.g., resource pools "A", "B", and "C").

Further, in one or more embodiments formation of the resource pools can serve to reserve computational resources 128 in accordance with the resource pool-to-clinical application 126 assignments. For example, a clinical application 126 assigned to resource pool A cannot employ computational resources 128 allocated to resource pool B. At least because high clinical priority clinical application 126 and/or persistent clinical applications 126 have reserved computational resources 128 via the resource pools, the resource pool component 302 can enable these clinical applications 126 to access their assigned allotment of computational resources 128 on-demand and with low activation latency. Further, clinical applications 126 can be executed simultaneously without experiencing a latency detriment. For instance, a persistent clinical application 126 running on resource pool C can be executed at the same time as a high clinical priority clinical application 126 running on resource pool A since the computational resources 128 allocated to resource pools A and C are distinct from each other.

Additionally, in one or more embodiments the computational capacity (e.g., as determined by computer capacity component 206 in accordance with various embodiments described herein) of each resource pool can be vary. For example, the resource pool component 302 can define the composition of computational resources 128 allocated to a resource pool based on the resources required (e.g., as determined by the required resources component 202 in accordance with various embodiments) to execute the high clinical priority clinical applications 126 or persistent clinical application 126 assigned to the resource pool. Thereby, the resource pool component 302 can assign clinical applications 126 to resource pools that have a sufficient allotment of computational resources 128 to facilitate execution.

In various embodiments, the resource pool component 302 can allocate overlapping computational resources 128 to a plurality of resource pools based on whether high clinical priority clinical applications 126 are expected to be run at the same time. For example, where a first high clinical priority clinical application 126 is unlikely to be executed at the same time as a second high clinical priority clinical application 126, a first resource pool assigned to the first high clinical priority clinical application 126 can share one or more computational resources 128 with a second resource pool assigned to the second high clinical priority clinical application 126. Since the first and second high clinical priority applications 126 are unlikely to be executed simultaneously, employment of the shared computational resources 128 during execution of the first high clinical priority clinical application 126 is unlikely to conflict with the execution of the second high clinical priority clinical application 126, and vice versa.

In one or more embodiments, the resource pool component 302 can determine the likelihood that a plurality of high clinical priority clinical applications 126 will be executed simultaneously based on a historic record of clinical application 126 executions. For example, the monitoring component 114 can generate an application log 304 that tracks when each clinical application 126 is executed by the one or more clinical computers 108 and/or how long each clinical application 126 ran during execution. The resource pool component 302 can analyze the application log 304 to determine how often given clinical applications 126 are run simultaneously, and thereby the resource pool component 302 can compute a likelihood value characterizing the probability that the given clinical applications 126 will be run simultaneously in the future. Where the likelihood value is below a defined threshold (e.g., defined via one or more input device 106), the resource pool component 302 can share one or more computational resources 128 between the resource pools assigned, or to be assigned, to the given clinical applications 126 (e.g., can allocate the same computational resource 128 to each of the resource pools associated with the given clinical applications 126). Where the likelihood value is greater than or equal to the defined threshold, the resource pool component 302 can ensure that different computational resources 128 are allocated to each of the resource pools assigned, or to be assigned, to the given clinical applications 126 (e.g., can ensure that the same computational resource 128 is not allocated to a plurality of the resource pools associated with the given clinical applications 126.

In one or more embodiments, the likelihood of given high clinical priority clinical applications 126 being run at the same time can be predefined. For example, likelihood values characterizing the probability that a given high clinical priority clinical application 126 will be run simultaneously with another high clinical priority clinical application 126 can be stored in the one or more memories 120. For instance, each high clinical priority clinical application 126 can be associated with a plurality of likelihood values, where each likelihood value from the plurality can characterize a respective combination of the given high clinical priority clinical application 126 with another high clinical priority clinical application 126.

In various embodiments, the resource pool component 302 can determine whether a computational resource 128 can be shared between two resource pools. For example, where a first high clinical priority clinical application 126 is assigned to resource pool A, and a second high clinical priority clinical application 126 is assigned to resource pool B; the resource pool component 302 can determine whether a computational resource 128 can be allocated to both resource pools A and B based on a likelihood value that characterizes the probability that the first high clinical priority clinical application 126 will need to be run at the same time as the second high clinical priority clinical applications 126. Additionally, in one or more embodiments the resource pool component 302 can determine whether a computational resource 128 can be shared between three or more resource pools. For example, where a first high clinical priority clinical application 126 is assigned to resource pool A, a second high clinical priority clinical application 126 is assigned to resource pool B, and a third high clinical priority clinical application 126 is assigned to resource pool C; the resource pool component 302 can determine whether a computational resource 128 can be allocated to all three resource pools A, B, and C based on a likelihood value that characterizes the probability that no two of the three high clinical priority clinical applications 126 will need to be run at the same time.

In various embodiments, the resource pool component 302 can allocate the same computational resource 128 to a plurality of resource pools (e.g., thereby rendering the computational resource 128 an overlapping resource) based on a high clinical priority clinical application's 126 under-utilization of the computational resource 128. For example, where a first high clinical priority application 126 utilizes less than one hundred percent of a given computational resource's 128 performance capacity during execution, the given computational resource 128 can also be allocated to a second resource pool assigned to a second high clinical priority clinical application 126 that also utilizes less than one hundred percent of the computational resource's 128 performance capacity during execution. For instance, a high clinical priority clinical application 126 can underutilize a CPU of the clinical computers 108 during execution due to a significant portion of the calculations being offloaded to a GPU and/or other accelerator. While the GPU and/or other accelerator performs the calculations, the CPU cores can be idle. During this idle period, the CPU cores can be employed to execute another high clinical priority clinical application 126. Thereby, an underutilized computational resource 128 can be shared by multiple resource pools without impeding execution of the respective high clinical priority clinical applications 126.

Additionally, the resource pool component 302 can define resource pools comprising both shared (e.g., overlapping) and exclusive (e.g., non-overlapping) computational resources 128. For example, where the resource pool component 302 allocates a plurality of computational resources 128 to a first resource pool, one or more of the computational resources 128 can be overlapping resources that are shared with another resource pool while one or more of the other computational resources 128 can be non-overlapping resources that are exclusively allocated to the first resource pool. For instance, a first high clinical priority CT image reconstruction clinical application 126 for a first CT scanner can employ a set of GPUs exclusively allocated to a first resource pool, but can also use a set of CPU cores shared with a second high clinical priority CT image reconstruction clinical application 126 for a second CT scanner (e.g., where the set of CPU cores is an overlapping computational resource allocated by the resource pool component 302 to both the first resource pool and a second resource pool).

In various embodiments, the resource pool component 302 can determine whether a computational resource 128 is underutilized by a clinical application 126 based on one or more determinations generated by the required resources component 202 and/or the computer capacity component 206. For example, the required resources component 202 can determine what the clinical applications 126 require from the computational resources 128 during execution. Further, the computer capacity component 206 can determine one or more characteristics of the computational resources 128 that are representative of the computational resources' 128 performance capacity. Differences between the total performance capacity available to a computational resource 128 and the computational requirements of clinical application 126 can be indicative of an underutilization of the computational resource 128 by the clinical application 126.

In various embodiments, the resource pool component 302 can further assign those non-persistent clinical applications 126 that do not have high clinical priority to the resource pools defined for the high clinical priority clinical applications 126 and/or persistent clinical applications 126. For example, the resource pool component 302 can establish the resource pools by defining: the number of resource pools based on the number of high clinical priority clinical applications 126 and/or persistent clinical applications 126; and the composition of the resource pools based on the computing requirements of the high clinical priority clinical applications 126 and/or persistent clinical applications 126 along with the computing capacity of the computational resources 128. Further, the resource pool component 302 can assign the remaining clinical applications 126 executable by the clinical computers 108 to the established resource pools. For instance, the remaining clinical applications 126 can be clinical applications 126 that are both: prioritized by the prioritization component 116 as having normal priority (e.g., clinical applications characterized by a priority value less than the defined threshold and/or labeled as "normal priority"); and are not persistent clinical applications 126 (e.g., are not persistently executed by the clinical computers 108 and/or have a low latency dependency). In one or more embodiments, the resource pool component 302 can assign to a resource pool: a high clinical priority clinical application 126 or a persistent clinical application 126; and one or more normal clinical priority, non-persistent clinical applications 126.

For example, the resource pool component 302 can assign to the same resource pool a clinical application 126 for stroke assessment using CT images, which can have a high clinical priority, and a clinical application 126 for removing motion artifacts in CT cardiac images, which can have a normal clinical priority. In another example, the resource pool component 302 can assign to the same resource pool a clinical application 126 for CT image reconstruction, which can have a high clinical priority, and a clinical application 126 for organ segmentation for radiation treatment, which can have a normal clinical priority.

In one or more embodiments, the resource pool component 302 can assign normal clinical priority, non-persistent clinical applications 126 to the resource pools based on a probability of the normal clinical priority, non-persistent clinical applications 126 requiring execution at the same time as the high clinical priority clinical application 126 or persistent clinical application 126 assigned to the given resource pool. For example, where a first high clinical priority clinical application 126 is assigned to a first resource pool, the resource pool component 302 can identify which of the normal clinical priority, non-persistent clinical applications 126 are least likely to be executed simultaneously with the first high clinical priority clinical application 126. Then the resource pool component 302 can assign one or more of the identified normal clinical priority, non-persistent clinical applications 126 to the first resource pool. Thereby, a probability that the computational resources 128 allocated to the first high clinical priority clinical application 126 is minimized at least because the one or more normal clinical priority, non-persistent clinical applications 126 assigned to the first resource pool are those least likely to be executed at the same time as the first high clinical priority clinical application 126.

In one or more embodiments, the resource pool component 302 can determine the likelihood that the respective high clinical priority clinical application 126 or persistent clinical application 126 of the given resource pool will be executed simultaneously with the one or more normal clinical priority, non-persistent clinical applications 126 based on a historic record of clinical application 126 executions. For example, the resource pool component 302 can analyze the application log 304 to determine how often given clinical applications 126 are run simultaneously, and thereby the resource pool component 302 can compute a likelihood value characterizing the probability that the given clinical applications 126 will be run simultaneously in the future. Where the likelihood value is below a defined threshold (e.g., defined via one or more input device 106), the resource pool component 302 can assign the clinical applications 126 to the same resource pool. Where the likelihood value is greater than or equal to the defined threshold, the resource pool component 302 can assign the clinical applications 126 to different resource pools.

In one or more embodiments, the likelihood of clinical applications 126 being run at the same time can be pre-defined. For example, likelihood values characterizing the probability that one or more normal clinical priority, non-persistent clinical application 126 will be run simultaneously with a high clinical priority clinical application 126 or persistent clinical application 126 can be stored in the one or more memories 120. For instance, each high clinical priority clinical application 126 can be associated with a plurality of likelihood values, where each likelihood value from the plurality can characterize a respective combination of the given high clinical priority clinical application 126 with another clinical application 126.

The number of clinical applications 126 assigned to a resource pool can depend on: the number of resource pools, the number of normal clinical priority, non-persistent clinical applications 126; and/or the probability of the high clinical priority applications 126 and/or persistent clinical applications 126 being executed at the same time as normal clinical priority, non-persistent clinical applications 126. Further, the number of clinical applications 126 per resource pool can vary. For example, a first resource pool can be assigned to more clinical applications 126 than one or more other resource pools. For instance, where a first resource pool is associated with a high clinical priority clinical application 126 that is rarely employed (e.g., as compared to the other high clinical priority clinical applications 126), and a second resource pool is associated with a high clinical priority clinical application 126 that is routinely employed (e.g., as compared to the other high clinical priority clinical applications 126); the resource pool component 302 can assign more normal clinical priority, non-persistent clinical applications 126 to the first resource pool than the second resource pool. Despite the first resource pool being assigned to more clinical applications 126, the likelihood that execution of the first high clinical priority clinical application 126 is in conflict with the execution of the one or more normal clinical priority, non-persistent clinical applications 126 can remain low at least due to the infrequency at which the first high clinical priority clinical application 126 is employed.

FIG. 4 illustrates a flow diagram of an example, non-limiting computer-implemented method 400 that can be employed by the resource pool component 302 to establish the resource pools and assign clinical applications 126 to the resource pools in accordance with one or more embodiments described herein. Repetitive description of like elements employed in other embodiments described herein is omitted for sake of brevity.

At 402, the computer-implemented method 400 can comprise determining (e.g., via resource pool component 302), by a system 100 operatively coupled to a processor 124, the number of high clinical priority clinical applications 126 and persistent clinical applications 126 that can be executed by the one or more clinical computers 108. In accordance with various embodiments described herein, the prioritization component 116 can delineate the clinical priority associated with each clinical applications 126 (e.g., via a priority value and/or a priority indicator). Those clinical applications 126 associated with a high clinical priority can be identified and/or counted by the resource pool component 302 at 402. Additionally, the resource pool component 302 can identify those clinical applications 126 that are persistently running the clinical computers 108 and require a low latency response to execution requests 125 (e.g., such as clinical applications 126 regarding high acuity patient monitoring, clinician image manipulation and analysis, and/or the like. The persistent clinical applications 126 can further be counted by the resource pool component at 402.

At 404, the computer-implemented method 400 can comprise defining (e.g., via resource pool component 302), by the system 100, a number of resource pools, where each resource pool can be assigned to a respective high clinical priority clinical application 126 or persistent clinical application 126. For example, the number of resource pools can be a function of the number of high clinical priority clinical applications 126 and persistent clinical applications 126 determined at 404 in accordance with various embodiments described herein. For instance, the total number of resource pools can be equivalent to the total number of high clinical priority clinical applications 126 and persistent clinical applications 126 that can be employed by the one or more clinical computers 108.

At 406, the computer-implemented method 400 can comprise determining (e.g., via required resources component 202 and/or resource pool component 302), by the system 100, the computational requirements of the high clinical priority clinical applications 126 and persistent clinical applications 126. At 408, the computer-implemented method 400 can comprise allocating (e.g., via resource pool component 302), by the system 100, computational resources 128 to each of the resource pools. For example, the resource pool component 302 can divide the computational resources 128 of the clinical computers 108 amongst the resource pools such that each resource pool has sufficient computational resources 128 to execute the assigned high clinical priority clinical application 126 or persistent clinical application 126.

In accordance with various embodiments, computational resources 128 allocated to a resource pool can be exclusive to the clinical applications 126 of the resource pool with limited exceptions. For example, the computational resources 128 allocated to resource pool A can be employed exclusively by the clinical applications 126 assigned to resource pool A such that clinical applications 126 assigned to other resource pools are not able to employ the computational resources 128 allocated to resource pool A. In accordance with various embodiments described herein, a first exception to the exclusivity of allocated computational resources 128 can be implemented by the resource pool component 302 where a high clinical priority clinical application 126 or persistent clinical application 126 of a first resource pool is unlikely to be executed at the same time as a high clinical priority clinical application 126 or persistent clinical application 126 of a second resource pool. Additionally, in accordance with various embodiments described herein, a second exception to the exclusivity of allocated computational resources 128 can be implemented by the resource pool component 302 where a high clinical priority clinical application 126 or persistent clinical application 126 underutilizes a computational resource 128. In the case of such exceptions, the resource pool component 302 can allocate the same computational resource 128 to both the first resource pool and the second resource pool. Thereby, allocation of the computational resource 128 can overlap between the first resource pool and the second resource pool such that the clinical applications 126 assigned to either resource pool can share the computational resource 128.

At 410, the computer-implemented method 400 can comprise assigning (e.g., via resource pool component 302), by the system 100, normal priority, non-persistent clinical applications 126 to the resource pools. In accordance with various embodiments described herein, the resource pool component 302 can assign the normal priority, non-persistent clinical applications 126 to the resource pools based on a probability that the normal priority, non-persistent clinical applications 126 will be executed at the same time as the high clinical priority clinical application 126 or persistent clinical application 126 of the given resource pool.

FIG. 5 illustrates a diagram of the example, non-limiting system 100 further comprising priority weight component 502 and/or preemption component 504 in accordance with one or more embodiments described herein. Repetitive description of like elements employed in other embodiments described herein is omitted for sake of brevity. In various embodiments, the priority weight component 502 and/or the preemption component 504 can control how the clinical applications 126 are executed within each resource pool. In one or more embodiments, the priority weight component 502 can set static or dynamic computational resource 128 priority weights to manage the order in which clinical applications 126 of the same resource pool employ the assigned computational resources 128. In one or more embodiments, the preemption component 504 can preempt the completion of one or more workloads (e.g., clinical applications 126) being executed on a given resource pool to fulfill an execution request 125 having higher clinical priority.

For example, the priority weight component 502 can set, with regards to each respective resource pool, static or dynamic computational resource 128 priority weights for each of the assigned clinical applications 126. The static or dynamic computational resource 128 priority weights can be mathematical values delineating relative shares of computing processing time on the assigned computational resources 128. For instance, the high clinical priority clinical application 126 or persistent application 126 of the resource pool can be assigned the highest weight value (e.g., a value of 2048) amongst the clinical applications 126 assigned to the resource pool. Further, the normal clinical priority, non-persistent clinical applications 126 assigned to the resource pool can be assigned lower weight values (e.g., a value of 1). For example, the high clinical priority clinical application 126 or persistent application 126 of a resource pool can be assigned a weight value of 2048 and the normal clinical priority, non-persistent clinical applications 126 of the resource pool can be assigned a weight value of 1; resulting in the high clinical priority clinical application 126 or persistent application 126 getting 2048 times the amount of processing time as the normal clinical priority, non-persistent clinical applications 126 in a given time duration.

In various circumstances, it can be preferred that execution requests 125 associated with high clinical priority be fulfilled as rapidly as possible by the clinical computers 108. For example, substantial improvements in patient care can be achieved when the full computational potential of the clinical computers 108 is leveraged to fulfill execution requests 125 associated with high clinical priority. For instance, high clinical priority can indicate a preference to minimize data collection and/or processing delays due to the negative implications said delays may have with regards to a medical treatment and/or diagnosis.

In one or more embodiments, the preemption component 504 can suspend and/or terminate the execution of one or more workloads (e.g., clinical applications 126) to free computational resources 128 for the fulfillment of a execution request 125 having a higher clinical priority. For instance, execution of a high clinical priority clinical application 126 or persistent clinical application of a resource pool can be inhibited by one or more normal clinical priority, non-persistent clinical applications 126 currently employing the computational resources of the resource pool. By preempting completion of the workloads, the preemption component 504 can free computational resources 128 of the resource pool to facilitate fulfillment of the execution request 125 having high clinical priority. Thereby, the preemption component 504 can avoid delays that would have otherwise been caused by waiting for the workloads to be completed and/or fulfilling the execution request 125 with less than the full computational capacity that can be achieved by the resource pool.

In various embodiments, the manner in which the preemption component 504 preempts completion of the operating normal clinical priority, non-persistent clinical applications 126 can depend on one or more determinations made by the resource allocation component 118. For example, whether the preemption component 504 suspends or terminates an operating clinical application 126 can depend on the computational capacity of the one or more clinical computers 108 (e.g., memory capacity and/or availability). In another example, how an operating normal clinical priority, non-persistent clinical application 126 is suspended can depend on one or more features enabled by the computational resources 128 (e.g., whether the clinical computers 108 can perform a memory sway and/or access virtual memory).

FIG. 6 illustrates a flow diagram of an example, non-limiting computer-implemented method 600 that can be implemented by the preemption component 504 in accordance with one or more embodiments described herein. Repetitive description of like elements employed in other embodiments described herein is omitted for sake of brevity.

At 602, the computer-implemented method 600 can comprise detecting (e.g., via monitoring component 114), by the system 100 operatively coupled to a processor 124, one or more execution requests 125 to be fulfilled on one or more clinical computers 108. In accordance with various embodiments described herein, the one or more execution requests 125 can be generated via one or more input devices 106. Additionally, the execution request 125 can direct the employment of one or more clinical applications 126 to perform one or more tasks that collect and/or process data in facilitation of a medical treatment, observation, and/or diagnosis.

At 604, the computer-implemented method 600 can comprise determining (e.g., via monitoring component 114), by the system 100, whether there is a workload currently being executed on the computational resources 128 of a given resource pool. For example, the clinical computers 108 can be performing one or more workloads (e.g., clinical applications 126) at a time in which the execution request is detected at 602. Wherein the computational resources 128 of the given resource pool are not executing a workload (e.g., not performing one or more normal clinical priority, non-persistent clinical applications 126), the computer-implemented method 600 can proceed to 606 and fulfill the execution request 125. At 606, the computer-implemented method 600 can employ (e.g., via the one or more clinical computers 108), by the system 100, one or more clinical applications 126 of the resource pool to facilitate fulfillment of the execution request 125. Where the clinical computers 108 are executing a workload (e.g., performing one or more clinical applications 126), the computer-implemented method 600 can proceed to 608. For instance, where the one or more computational resources 128 of a given resource pool are being employed by one or more clinical applications 126.

At 608, the computer-implemented method 600 can comprise determining (e.g., via prioritization component 116), by the system 100, whether the one or more execution requests 125 have higher clinical priority than the workload currently being executed. For instance, step 608 can comprise determining whether the one or more execution requests 125 are associated with a clinical application 126 having higher clinical priority than the clinical application 126 currently employing the computational resources of the resource pool. In accordance with various embodiments described herein, the prioritization component 116 can compare the clinical priority of the execution request 125 with the clinical priority of the operating workload. Where the operating workload has the higher clinical priority (e.g., where the operating clinical application 126 is the high clinical priority clinical application 126 or the persistent clinical application 126 of the resource pool), the computer-implemented method 600 can proceed to 610. At 610, the system 100 can proceed to implement computer-implemented method 700 (e.g., depicted in FIG. 7), which can complete execution of the operating workload and re-assess the one or more execution requests 125. Where the one or more execution requests 125 have the higher clinical priority (e.g., where the operating clinical application 126 is a normal clinical priority, non-persistent clinical application 126 and the one or more execution requests 125 are associated with the high clinical priority clinical application 126 or the persistent clinical application 126 of the resource pool), the computer-implemented method 600 can proceed to 612.

At 612, the computer-implemented method 600 can comprise determining (e.g., via resource allocation component 118), by the system 100, whether the one or more clinical computers 108 have adequate computational resources 128 for workload suspension and memory storage. For instance, step 612 can comprise determining whether the one or more computational resources 128 of the given resource pool enable workload suspension and memory storage. In accordance with various embodiments described herein, the resource allocation component 118 can determine whether the computational resources 128 accessible to the clinical applications 126 of the resource pool are able to suspend the workload currently being executed. Additionally, wherein adequate computational resources 128 for workload suspension are available, the resource allocation component 118 can further determine whether the one or more computational resources 128 accessible to the resource pool include adequate memory to store the progress of the suspended workload. For example, the resource allocation component 118 (e.g., via required resources component 202, available resources component 204, and/or computer capacity component 206) can determine: whether there is enough free system memory available on the accessible computational resources 128 to store memory of the suspended workload and fulfill the execution request 125; whether a memory swap operation is an enabled feature of the one or more accessible computational resources 128; and/or whether the accessible computational resources 128 can utilize virtual memory to facilitate data storage requirements. For instance, at 612 the computer-implemented method 600 can determine whether the computational resources 128 assigned to the given resource pool include one or more accelerators (e.g., GPUs) capable of performing memory page swapping to meet the memory storage requirements.

In response to a determination at 612 that the one or more computational resources 128 assigned to the given resource pool are able to suspend the workload and have adequate memory storage to facilitate the suspension; the computer-implemented method 600 can proceed to 614. At 614, the system 100 can proceed to implement computer-implemented method 800 (e.g., depicted in FIG. 8), which can preempt completion of the workload via a workload suspension technique in favor of expedited fulfillment of the execution request 125. For instance, the computer-implemented method 600 can proceed to 614 in response to determining that fulfillment of the high clinical priority execution request 125 would only utilize CPU resources and there is enough free system memory available at the one or more clinical computers 108 to keep memory of the suspended workload, or perform a memory swap of the suspended workload, while fulfilling the execution request 125. In another instance, the computer-implemented method 600 can proceed to 614 in response to determining that fulfillment of the execution request 125 would utilize CPU and accelerator (e.g., GPU) resources and there is enough free system memory on the one or more clinical computers 108 to keep memory of the suspended workload and all memory pages allocated by the suspended workload on the one or more accelerator devices while fulfilling the execution request 125. In a further instance, the computer-implemented method 600 can proceed to 614 in response to determining that fulfillment of the execution request 125 would utilize CPU and accelerator (e.g., GPU) resources and the one or more assigned computational resources 128 support an accelerator memory oversubscription and virtual memory page swap.

In response to a determination at 612 that the resource pool does not include computational resources 128 that are able to suspend the workload or adequate memory storage to facilitate the suspension; the computer-implemented method 600 can proceed to 616. At 616, the computer-implemented method 600 can comprise determining (e.g., via resource allocation component 118), by the system 100, whether the one or more assigned computational resources 128 have enable workload suspension along with memory eviction and loading capacities. For instance, at 616 the computer-implemented method 600 can determine whether the accessible computational resources 128 include one or more accelerators (e.g., GPUs) capable of performing on-demand memory eviction and loading to meet the memory storage requirements. For example, wherein fulfillment of the execution request 125 would utilize accelerator (e.g., GPU) resources, but the one or more one or more assigned computational resources 128 neither have sufficient free memory storage, nor support accelerator memory oversubscription and virtual memory page swap; the computer-implemented method 600 at 616 can determine (e.g., via resource allocation component 118, including computer capacity component 206) whether one or more clinical computers 108 do support accelerator memory on-demand eviction and loading.

In response to determining that the accessible computational resources 128 do support workload suspension and on-demand memory eviction and loading, the computer-implemented method 600 can proceed to 618. At 618, the system 100 can proceed to implement computer-implemented method 900 (e.g., depicted in FIG. 9), which can preempt completion of the workload via a workload suspension technique in favor of expedited fulfillment of the execution request 125. In response to determining that the accessible computational resources 128 do not support workload suspension or do not support on-demand memory eviction and loading, the computer-implemented method 600 can proceed to 620. At 620, the system 100 can proceed to implement computer-implemented method 1000 (e.g., depicted in FIG. 10), which can preempt completion of the workload via termination of the workload execution in favor of expedited fulfillment of the execution request 125.

Figure 7:
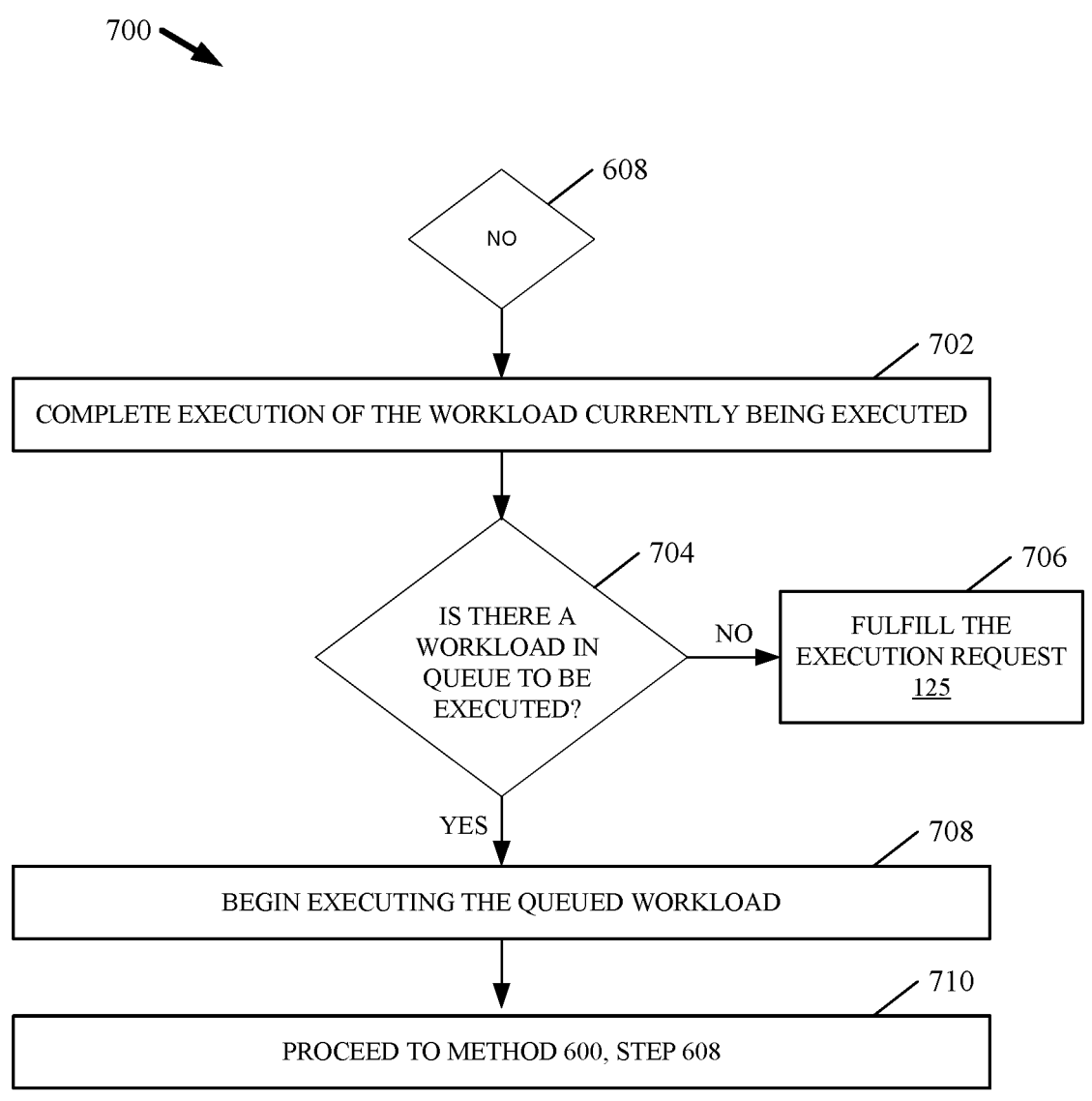
FIG. 7 illustrates a flow diagram of an example, non-limiting computer-implemented method that can facilitate managing execution of various clinical applications based on available computational resources and clinical priority in accordance with one or more embodiments described herein.

FIG. 7 illustrates a flow diagram of example, non-limiting computer-implemented method 700 that can be implemented by the preemption component 504 to manage multiple workload requests directed to the same resource pool in accordance with one or more embodiments described herein. Repetitive description of like elements employed in other embodiments described herein is omitted for sake of brevity. As shown in FIG. 7, computer-implemented method 700 can be implemented by the system 100 in response to a "no" determination at 608 of computer-implemented method 600. For example, computer-implemented method 700 can be implemented by the system 100 when an execution request 125 has lower, or equal, clinical priority than a workload currently employing the computational resources 128 of the resource pool.

At 702, the computer-implemented method 700 can comprise completing (e.g., via the one or more clinical computers 108), by the system 100, execution of the workload currently being executed. Upon completion of the workload, the computer-implemented method 700 can proceed to 704 to re-assess the execution request 125.

At 704, the computer-implemented method 700 can comprise determining (e.g., via monitoring component 114), by the system 100, whether there is another workload in queue to be executed using the computational resources 128 of the given resource pool. For example, there can one or more additional workloads awaiting fulfillment by the one or more computational resources 128 of the resource pool. Where one or more additional workloads are not queued, the computer-implemented method 700 can proceed to 706 and fulfill the execution request 125. At 706, the computer-implemented method 700 can employ (e.g., via the one or more clinical computers 108), by the system 100, one or more clinical applications 126 to facilitate fulfillment of the execution request 125. Where the one or more additional workloads are queued, the computer-implemented method 700 can proceed to 708.

At 708, the computer-implemented method 700 can comprise beginning (e.g., via one or more clinical computers 108), by the system 100, execution of the one or more queued workloads. Further, at 710 the computer-implemented method 700 can comprise proceeding to step 608 of computer-implemented method 600. For example, at 608 the execution request 125 can be re-evaluated to determine whether the execution request 125 has a higher clinical priority that the previously queued workload, which is now the workload currently being executed. Thereby, the execution request 125 can continued to be processed in accordance with computer-implemented method 600.

Figure 8:
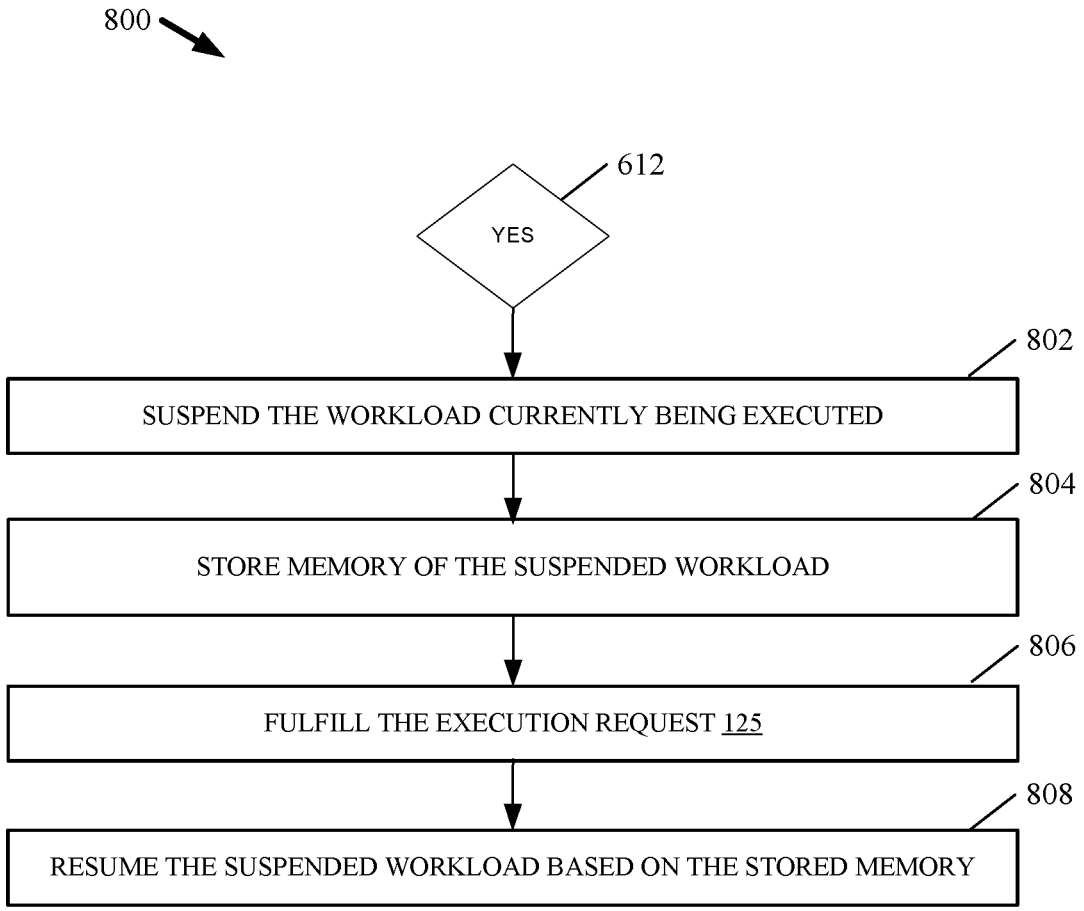
FIG. 8 illustrates a flow diagram of an example, non-limiting computer-implemented method that can facilitate managing execution of various clinical applications based on available computational resources and clinical priority in accordance with one or more embodiments described herein.

FIG. 8 illustrates a flow diagram of example, non-limiting computer-implemented method 800 that can be implemented by the preemption component 504 to facilitate preemption of one or more workloads (e.g., one or more operating normal clinical priority, non-persistent clinical applications 126) to fulfill one or more high clinical priority execution requests 125 in accordance with one or more embodiments described herein. Repetitive description of like elements employed in other embodiments described herein is omitted for sake of brevity. As shown in FIG. 8, computer-implemented method 800 can be implemented by the system 100 in response to a "yes" determination at 612 of computer-implemented method 600. For example, computer-implemented method 800 can be implemented by the system 100 when: an execution request 125 has a higher clinical priority than a workload currently being completed on the one or more computational resources 128 of the resource pool, the accessible computational resources 128 enable workload suspensions; and the accessible computational resources 128 have adequate memory storage capabilities.

At 802, the computer-implemented method 800 can comprise suspending (e.g., via preemption component 504), by the system 100, the one or more workloads currently being executed on the one or more clinical computers 108. Thereby, the system 100 can preempt completion of the workloads and free the computational resources 128 of the resource pool for fulfillment of the execution request 125. At 804, the computer-implemented method 800 can comprise storing memory of the suspended workloads to facilitate later resumption. For example, wherein fulfillment of the execution request 125 requires CPU resources and not accelerator resources; the preemption component 504 can direct memory of the suspended workload be stored on the accessible computational resources 128. In another example, where fulfillment of the execution request 125 requires CPU and accelerator resources; the preemption component 504 can direct an accelerator memory oversubscription and virtual memory page swap to facilitate storing memory of the suspended workloads.

At 806, the computer-implemented method 800 can employ (e.g., via the one or more clinical computers 108), by the system 100, one or more clinical applications 126 to facilitate fulfillment of the execution request 125. Subsequent to completing the execution request 125, the computer-implemented method 800 can proceed to 808. At 808, the computer-implemented method 800 can comprise resuming the suspended workload based on the stored memory.

Figure 9:
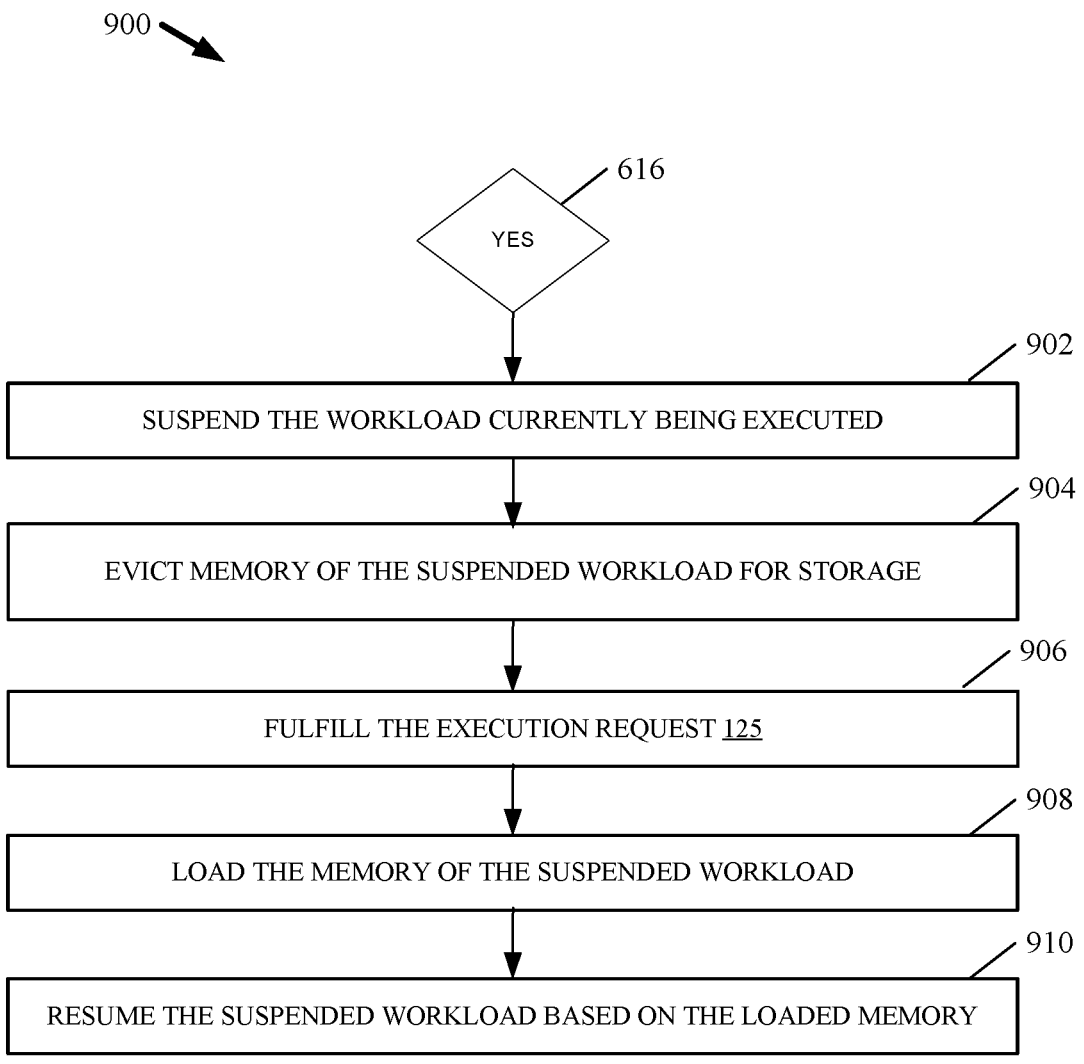
FIG. 9 illustrates a flow diagram of an example, non-limiting computer-implemented method that can facilitate managing execution of various clinical applications based on available computational resources and clinical priority in accordance with one or more embodiments described herein.

FIG. 9 illustrates a flow diagram of example, non-limiting computer-implemented method 900 that can facilitate preemption of one or more workloads to fulfill one or more high clinical priority execution requests 125 in accordance with one or more embodiments described herein. Repetitive description of like elements employed in other embodiments described herein is omitted for sake of brevity. As shown in FIG. 9, computer-implemented method 900 can be implemented by the system 100 in response to a "yes" determination at 616 of computer-implemented method 600. For example, computer-implemented method 900 can be implemented by the system 100 when: an execution request 125 has a higher clinical priority than a workload currently being completed on the computational resources 128 of the given resource pool, the accessible computational resources 128 enable workload suspensions; and the accessible computational resources 128 have does not adequate memory storage capabilities, but does support memory on-demand eviction and loading protocols.

At 902, the computer-implemented method 900 can comprise suspending (e.g., via preemption component 504), by the system 100, the one or more workloads currently being executed on the one or more clinical computers 108. Thereby, the system 100 can preempt completion of the workloads and free the computational resources 128 of the clinical computers 108 for fulfillment of the execution request 125. At 904, the computer-implemented method 900 can comprise evicting memory of the one or more suspended workloads for storage. For example, one or more accelerators of the clinical computers 108 can evict one or more memory pages of the suspended workload to one or more external memory devices (e.g., memory 120) for storage outside the clinical computers 108.

At 906, the computer-implemented method 900 can employ (e.g., via the one or more clinical computers 108), by the system 100, one or more clinical applications 126 to facilitate fulfillment of the execution request 125. Subsequent to completing the execution request 125, the computer-implemented method 900 can proceed to 908. At 908, the computer-implemented method 900 can comprise loading the memory of the one or more suspended workloads that was evicted at 904. For example, the accessible computational resources 128 can comprise one or more accelerators that can load one or more memory pages of the suspended workload. At 910, the computer-implemented method 900 can resume the one or more suspended workloads based on the memory loaded at 908.

Figure 10:
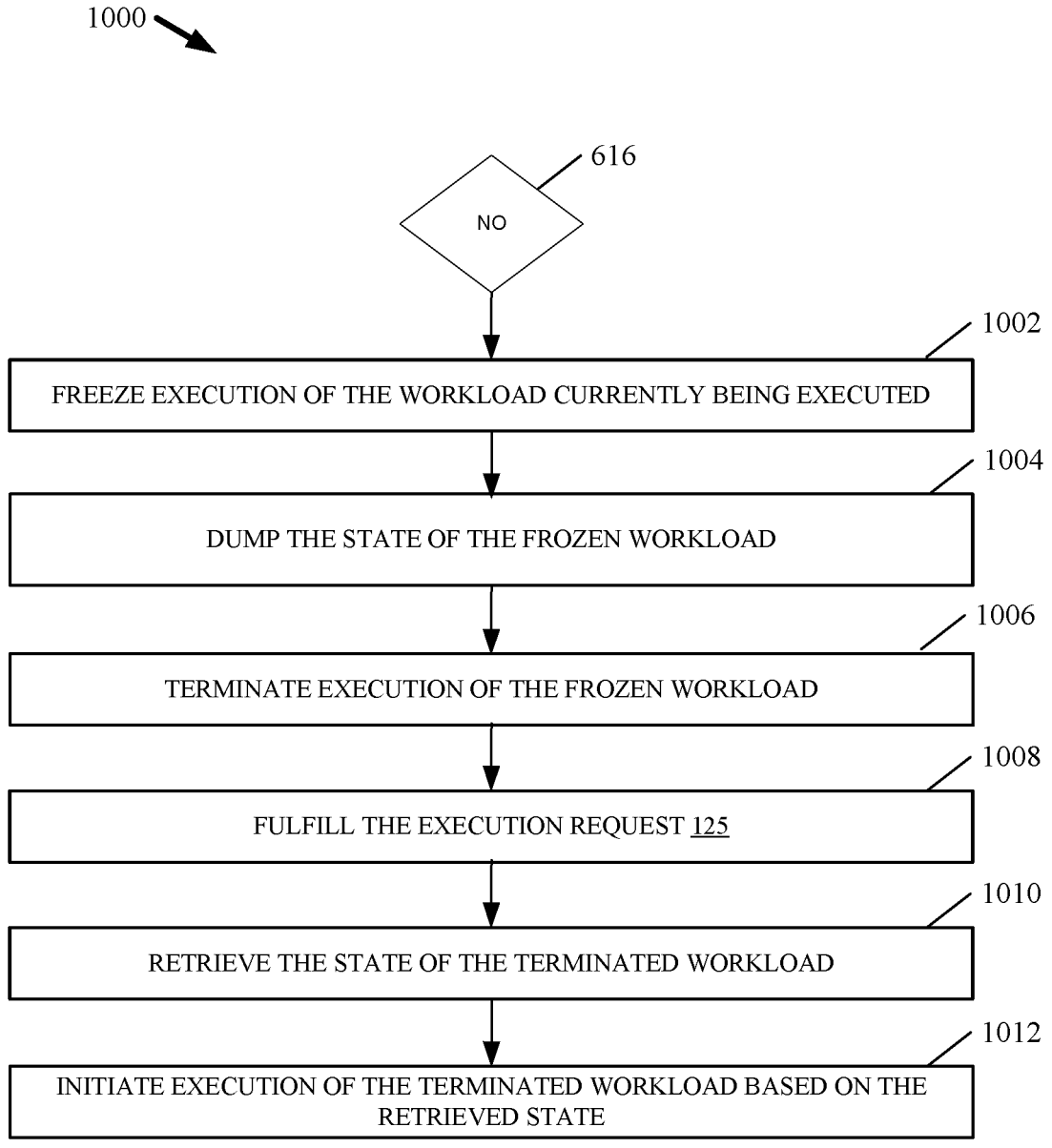
FIG. 10 illustrates a flow diagram of an example, non-limiting computer-implemented method that can facilitate managing execution of various clinical applications based on available computational resources and clinical priority in accordance with one or more embodiments described herein.

FIG. 10 illustrates a flow diagram of example, non-limiting computer-implemented method 1000 that can be implemented by the preemption component 504 to facilitate preemption of one or more workloads to fulfill one or more high clinical priority execution requests 125 in accordance with one or more embodiments described herein. Repetitive description of like elements employed in other embodiments described herein is omitted for sake of brevity. As shown in FIG. 10, computer-implemented method 1000 can be implemented by the system 100 in response to a "no" determination at 616 of computer-implemented method 600. For example, computer-implemented method 1000 can be implemented by the system 100 when: an execution request 125 has a higher clinical priority than a workload currently being completed on the accessible computational resources 128, but the accessible computational resources 128 are unable to support a workload suspension.

At 1002, the computer-implemented method 1000 can comprise freezing (e.g., via preemption component 504), by the system 100, the one or more workloads currently being executed on the one or more clinical computers 108. At 1004, the computer-implemented method 1000 can comprise dumping (e.g., via the one or more clinical computers 108) the state of the one or more frozen workloads. In various embodiments, the one or more clinical computers 108 can dump the workload state periodically and/or on-demand prior to terminations. Further, at 1006 the computer-implemented method 1000 can comprise terminating (e.g., via the one or more clinical computers 108) execution of the one or more frozen workloads. Thereby, the system 100 can preempt completion of the workloads and free the computational resources 128 of the resource pool for fulfillment of the execution request 125.

At 1008, the computer-implemented method 1000 can employ (e.g., via the one or more clinical computers 108), by the system 100, one or more clinical applications 126 to facilitate fulfillment of the execution request 125. Subsequent to completing the execution request 125, the computer-implemented method 1000 can proceed to 1010. At 1010, the computer-implemented method 1000 can comprise retrieving (e.g., via the one or more clinical computers 108), by the system 100, the state of the one or more terminated workloads. For example, the one or more clinical computers 108 can retrieve the workload state dumped at 1004. At 1012, the computer-implemented method 1000 can comprise initiating (e.g., via the accessible computational resources 128), by the system 100, execution of the one or more terminated workloads based on the retrieved state.

Figure 11:
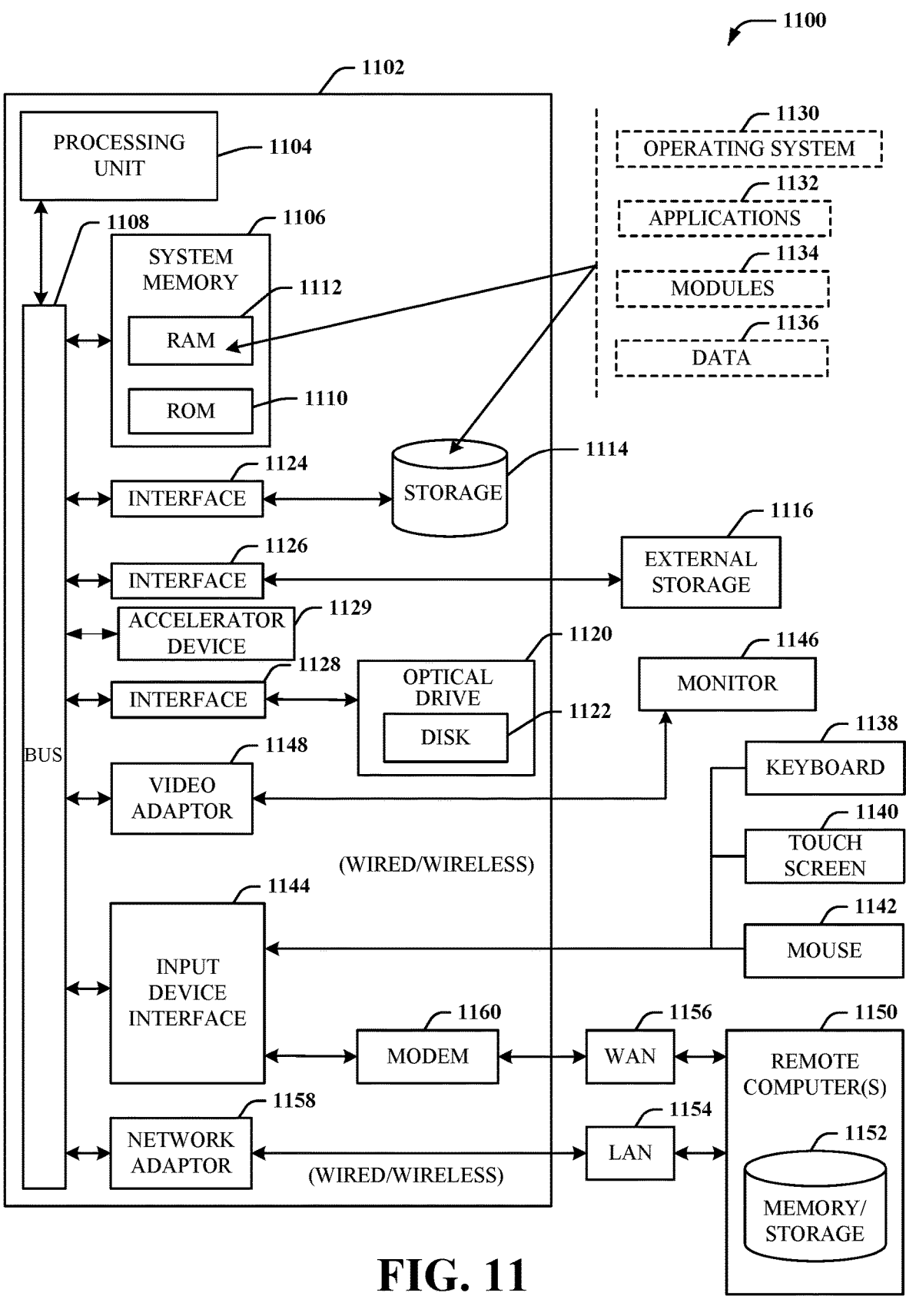
FIG. 11 illustrates a block diagram of an example, non-limiting operating environment in which one or more embodiments described herein can be facilitated.

In order to provide additional context for various embodiments described herein, FIG. 11 and the following discussion are intended to provide a brief, general description of a suitable computing environment 1100 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things ("IoT") devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory ("RAM"), read only memory ("ROM"), electrically erasable programmable read only memory ("EEPROM"), flash memory or other memory technology, compact disk read only memory ("CD-ROM"), digital versatile disk ("DVD"), Blu-ray disc ("BD") or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, the example environment 1100 for implementing various embodiments of the aspects described herein includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures can also be employed as the processing unit 1104.

The system bus 1108 can be any of several types of bus structure that can further interconnect to a memory bus (with or without a memory controller), a peripheral bus, and a local bus using any of a variety of commercially available bus architectures. The system memory 1106 includes ROM 1110 and RAM 1112. A basic input/output system ("BIOS") can be stored in a non-volatile memory such as ROM, erasable programmable read only memory ("EPROM"), EEPROM, which BIOS contains the basic routines that help to transfer information between elements within the computer 1102, such as during startup. The RAM 1112 can also include a high-speed RAM such as static RAM for caching data.

The computer 1102 further includes storage 1114 (e.g., an internal hard disk drive ("HDD"), including EIDE, SATA), one or more external storage devices 1116 (e.g., a magnetic floppy disk drive ("FDD") 1116, a memory stick or flash drive reader, a memory card reader, etc.) and an optical disk drive 1120 (e.g., which can read or write from a CD-ROM disc, a DVD, a BD, etc.). While the storage 1114 is illustrated as located within the computer 1102, the storage 1114 can also be configured for external use in a suitable chassis (not shown). Additionally, while not shown in environment 1100, a solid state drive ("SSD") could be used in addition to, or in place of, storage 1114. The storage 1114, external storage device(s) 1116 and optical disk drive 1120 can be connected to the system bus 1108 by interface 1124, an external storage interface 1126 and an optical drive interface 1128, respectively. The interface 1124 for external drive implementations can include at least one or both of Universal Serial Bus ("USB") and Institute of Electrical and Electronics Engineers ("IEEE") 13114 interface technologies. Other external drive connection technologies are within contemplation of the embodiments described herein. Additionally, the example environment 1100 can include one or more accelerator devices 11211, such as GPUs, connected to system bus 1108.

The drives and their associated computer-readable storage media provide nonvolatile storage of data, data structures, computer-executable instructions, and so forth. For the computer 1102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. The systems and methods described herein can be implemented utilizing various commercially available operating systems or combinations of operating systems.

Computer 1102 can optionally comprise emulation technologies. For example, a hypervisor (not shown) or other intermediary can emulate a hardware environment for operating system 1130, and the emulated hardware can optionally be different from the hardware illustrated in FIG. 11. In such an embodiment, operating system 1130 can comprise one virtual machine ("VM") of multiple VMs hosted at computer 1102. Furthermore, operating system 1130 can provide runtime environments, such as the Java runtime environment or the .NET framework, for applications 1132. Runtime environments are consistent execution environments that allow applications 1132 to run on any operating system that includes the runtime environment. Similarly, operating system 1130 can support containers, and applications 1132 can be in the form of containers, which are lightweight, standalone, executable packages of software that include, e.g., code, runtime, system tools, system libraries and settings for an application.

Further, computer 1102 can be enable with a security module, such as a trusted processing module ("TPM"). For instance with a TPM, boot components hash next in time boot components, and wait for a match of results to secured values, before loading a next boot component. This process can take place at any layer in the code execution stack of computer 1102, e.g., applied at the application execution level or at the operating system ("OS") kernel level, thereby enabling security at any level of code execution.

A user can enter commands and information into the computer 1102 through one or more wired/wireless input devices, e.g., a keyboard 1138, a touch screen 1140, and a pointing device, such as a mouse 1142. Other input devices (not shown) can include a microphone, an infrared ("IR") remote control, a radio frequency ("RF") remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1104 through an input device interface 1144 that can be coupled to the system bus 1108, but can be connected by other interfaces, such as a parallel port, an IEEE 13114 serial port, a game port, a USB port, an IR interface, a BLUETOOTH® interface, etc.

A monitor 1146 or other type of display device can be also connected to the system bus 1108 via an interface, such as a video adapter 1148. In addition to the monitor 1146, a computer typically includes other peripheral output devices (not shown), such as speakers, printers, etc.

The computer 1102 can operate in a networked environment using logical connections via wired and/or wireless communications to one or more remote computers, such as a remote computer(s) 1150. The remote computer(s) 1150 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1152 is illustrated. The logical connections depicted include wired/wireless connectivity to a local area network ("LAN") 1154 and/or larger networks, e.g., a wide area network ("WAN") 1156. Such LAN and WAN networking environments are commonplace in offices and companies, and facilitate enterprise-wide computer networks, such as intranets, all of which can connect to a global communications network, e.g., the Internet.

When used in a LAN networking environment, the computer 1102 can be connected to the local network 1154 through a wired and/or wireless communication network interface or adapter 1158. The adapter 1158 can facilitate wired or wireless communication to the LAN 1154, which can also include a wireless access point ("AP") disposed thereon for communicating with the adapter 1158 in a wireless mode.

When used in a WAN networking environment, the computer 1102 can include a modem 1160 or can be connected to a communications server on the WAN 1156 via other means for establishing communications over the WAN 1156, such as by way of the Internet. The modem 1160, which can be internal or external and a wired or wireless device, can be connected to the system bus 1108 via the input device interface 1144. In a networked environment, program modules depicted relative to the computer 1102 or portions thereof, can be stored in the remote memory/storage device 1152. It will be appreciated that the network connections shown are example and other means of establishing a communications link between the computers can be used.

When used in either a LAN or WAN networking environment, the computer 1102 can access cloud storage systems or other network-based storage systems in addition to, or in place of, external storage devices 1116 as described above. Generally, a connection between the computer 1102 and a cloud storage system can be established over a LAN 1154 or WAN 1156 e.g., by the adapter 1158 or modem 1160, respectively. Upon connecting the computer 1102 to an associated cloud storage system, the external storage interface 1126 can, with the aid of the adapter 1158 and/or modem 1160, manage storage provided by the cloud storage system as it would other types of external storage. For instance, the external storage interface 1126 can be configured to provide access to cloud storage sources as if those sources were physically connected to the computer 1102.

The computer 1102 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity ("Wi-Fi") and BLUETOOTH® wireless technologies. Thus, the communication can be a predefined structure as with a conventional network or simply an ad hoc communication between at least two devices.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

What is claimed is:

1. A system, comprising:
  a processor that executes computer-executable components stored in a memory, wherein the computer-executable components comprise:
    a prioritization component that determines respective clinical priorities of respective applications; and
    a resource allocation component, wherein, in response to the prioritization component determining, based on the respective clinical priorities, that a first workload to be executed by a first application utilizing a subgroup of computational resources of a resource pool has a higher priority than a second workload being executed by a second application utilizing the subgroup of computational resources, the resource allocation component determines whether the subgroup of computational resources comprises sufficient available memory space in the memory to perform a memory page swap to store memory pages of data relating to the second workload in the memory during execution of the first workload, based on an amount of available memory space in the memory determined based on tracking of the available memory space, and wherein completion of execution of the second workload is preempted to enable expedited execution of the first workload based on a preemption technique, the preemption technique determined based on the determination of whether the subgroup of computational resources comprises the sufficient available memory space in the memory to perform the memory page swap.

2. The system of claim 1, wherein the memory comprises at least one of a virtual memory, a physical memory, or an accelerator memory, wherein the memory comprises an internal memory within a device that comprises the processor or an external memory that is external to the device, and wherein the memory page swap comprises a virtual memory page swap.

3. The system of claim 1, wherein the prioritization component determines the respective clinical priorities of the respective applications based on respective tasks performed or to be performed by the respective applications, wherein the respective clinical priorities characterize respective time sensitivities of the respective tasks, wherein the respective tasks comprise a first group of tasks performed or to be performed by the first application and a second group of tasks performed or to be performed by the second application, wherein the respective clinical priorities comprise a first clinical priority associated with the first group of tasks and a second clinical priority associated with the second group of tasks, wherein the prioritization component, employing a machine learning model, performs a first machine learning-based analysis of previous clinical priorities and previous parameters associated with previous tasks associated with at least some of the respective applications to facilitate learning to identify or determine the first clinical priority associated with the first group of tasks or the second clinical priority associated with the second group of tasks, wherein some of the previous parameters relate to previous time sensitivities associated with the previous tasks, and wherein the prioritization component, employing the machine learning model, identifies or determines the first clinical priority associated with the first group of tasks or the second clinical priority associated with the second group of tasks based on a result of performance of a second machine learning-based analysis of parameters associated with the first group of tasks or the second group of tasks.

4. The system of claim 1, wherein the memory page swap comprises a virtual memory page swap, and wherein the preemption technique comprises or relates to a workload preemption technique, a workload suspension technique, a memory eviction technique, a memory page loading technique, the virtual memory page swap, or an accelerator memory oversubscription technique.

5. The system of claim 1, wherein the computer-executable components further comprise a preemption component that, in response to a determination that the subgroup of computational resources comprises the sufficient available memory space in the memory to perform the memory page swap, preempts the completion of the execution of the second workload by suspension of the execution of the second workload to enable the expedited execution of the first workload by the first application utilizing the subgroup of computational resources, and directs performance of the memory page swap to store the memory pages of data in the memory during the suspension.

6. The system of claim 5, wherein the preemption component expedites the execution of the first workload by the suspension of the execution of the second workload and a direction of the performance of the memory page swap to store the memory pages of data in the memory during the suspension to enable execution of one or more tasks of the first workload, and wherein, after the execution of the one or more tasks, the second workload is resumed utilizing the subgroup of computational resources based on the memory pages of data that were stored in and retrieved from the memory.

7. The system of claim 6, wherein the memory pages of data relating to the second workload comprise workload-related data relating to the execution, and progress towards completion, of the second workload up to a point of the suspension of the second workload.

8. The system of claim 1, wherein the subgroup of computational resources comprises a processor unit and an accelerator processor unit, and wherein the resource allocation component determines that the memory page swap is able to be performed to facilitate a preemption of the completion of the execution of the second workload based on determining that the subgroup of computational resources supports an accelerator memory oversubscription associated with the accelerator processor unit and the memory page swap.

9. The system of claim 1, wherein the resource allocation component determines whether the subgroup of computational resources comprises a processor unit and an accelerator processor unit, and, in response to determining that the subgroup of computational resources comprises the processor unit and the accelerator processor unit, the resource allocation component determines an amount of the memory, comprising a physical memory, a virtual memory, or an accelerator memory, that the processor unit or the accelerator processor unit has available to store the memory pages of data relating to the second workload during the preemption, comprising suspension of the execution, of the second workload.

10. The system of claim 1, wherein the computer-executable components further comprise a resource pool component that divides a group of computational resources across a group of resource pools, comprising the resource pool, and assigns the respective applications to respective resource pools of the group of resource pools based on the respective clinical priorities, and wherein the resource pool component assigns the first application and the second application to the resource pool that comprises the subgroup of the group of computational resources.

11. The system of claim 10, wherein the respective applications further comprise a third application, wherein the resource pool is a first resource pool, wherein the group of resource pools comprises the first resource pool and a second resource pool, wherein the resource pool component assigns the third application to the second resource pool, wherein the resource pool component determines whether a computational resource of the group of computational resources is to be shared by the first resource pool and the second resource pool based on a result of a determination of whether a likelihood value associated with the first application and the third application satisfies a defined threshold likelihood value, wherein the likelihood value indicates a probability that the first application will be executed at a same time as the third application, and wherein, in response to determining that the likelihood value does not satisfy the defined threshold likelihood value, the resource pool component determines that the computational resource is not to be shared by the first resource pool and the second resource pool.

12. The system of claim 10, wherein the respective applications further comprise a third application, wherein the resource pool is a first resource pool, wherein the group of resource pools comprises the first resource pool and a second resource pool, wherein the resource pool component assigns the third application to the second resource pool, wherein the resource pool component determines whether a computational resource of the computational resources is to be shared by the first resource pool and the second resource pool based on a result of a determination of whether a likelihood value associated with the first application and the third application satisfies a defined threshold likelihood value, wherein the likelihood value indicates a probability that the first application will be executed at a same time as the third application, and wherein, in response to determining that the likelihood value satisfies the defined threshold likelihood value, the resource pool component determines that the computational resource is to be shared by the first resource pool and the second resource pool.

13. A method, comprising:

identifying, by a system operably coupled to a processor, respective clinical priorities of respective tasks;

in response to identifying, based on the respective clinical priorities, that first tasks of a first workload to be executed by a first application utilizing a group of computational resources have a greater priority than second tasks of a second workload being executed by a second application utilizing the group of computational resources, determining, by the system, whether the group of computational resources comprises sufficient available memory space in a memory to perform a memory page swap to store memory pages of information relating to the second workload in the memory during execution of the first tasks of the first workload, based on tracking of the available memory space in the memory; and expediting, by the system, execution of the first tasks of the first workload by preempting completion of execution of the second tasks of the second workload based on the respective clinical priorities and based on a preemption process, the preemption process determined based on a result of the determining of whether the group of computational resources comprises the sufficient available memory space in the memory to perform the memory page swap.

14. The method of claim 13, wherein the memory comprises at least one of a virtual memory, a physical memory, or an accelerator memory, and wherein the memory page swap comprises a virtual memory page swap.

15. The method of claim 13, further comprising:

based on the result indicating that the group of computational resources comprises the sufficient available memory space in the memory to perform the memory page swap, controlling, by the system, at least one computational resource of the group of computational resources to have the at least one computational resource perform the memory page swap to store the memory pages of information relating to the second workload in the memory in connection with the preempting to facilitate the execution of the first tasks.

16. The method of claim 15, further comprising:

in connection with the preempting, suspending, by the system, execution of the second tasks of the second workload, wherein the memory pages of information are stored in the sufficient available memory space in the memory;

executing, by the system, the first tasks of the first workload utilizing the group of computational resources;

retrieving, by the system, the memory pages of information relating to the second workload from the memory; and based on the memory pages of information, resuming, by the system, the execution of the second tasks of the second workload utilizing the group of computational resources.

17. The method of claim 13, wherein the respective applications comprise a third application, wherein the group of computational resources is a first group of computational resources, wherein the respective clinical priorities characterize respective time sensitivities of the respective tasks, and wherein the method further comprises:

assigning, by the system, respective applications to respective resource pools based on the respective clinical priorities, wherein the respective resource pools comprise a first resource pool comprising the first group of computational resources and a second resource pool comprising a second group of computational resources, wherein the assigning comprises assigning the first application and the second application to the first resource pool and the third application to the second resource pool;

determining, by the system, that there is an underutilization of a computational resource by the third application; and based on determining that there is the underutilization of the computational resource by the third application, determining, by the system, that the computational resource is to be shared by the first resource pool and the second resource pool.

18. A computer program product for managing resources, the computer program product comprising a non-transitory computer-readable medium having program instructions embodied therewith, the program instructions executable by a processor to cause the processor to:

determine a first clinical priority of first tasks of a first workload to be executed by a first application utilizing a group of resources and a second clinical priority of second tasks of a second workload being executed by a second application utilizing the group of resources;

in response to determining, based on the first clinical priority and the second clinical priority, that the first tasks have a higher priority than the second tasks, determine whether the group of resources comprises available data storage locations in a memory that are able to be utilized to perform a memory page swap to store memory pages of data relating to the second workload in the memory during execution of the first tasks of the first workload, based on tracking of the available data storage locations in the memory; and expedite fulfillment of execution of the first tasks by preempting completion of execution of the second tasks based on the first clinical priority and based on a preemption technique, wherein the preemption technique is determined based on a result of the determining of whether the group of resources comprises the available data storage locations in the memory that are able to be utilized to perform the memory page swap.

19. The computer program product of claim 18, wherein the program instructions further cause the processor to:

based on the result indicating that the group of resources comprises the available data storage locations in the memory to perform the memory page swap, instruct at least one resource of the group of resources to perform the memory page swap to store the memory pages of data relating to the second workload in the available data storage locations in the memory in connection with the preempting to facilitate the execution of the first tasks, wherein the memory page swap comprises a virtual memory page swap.

20. The computer program product of claim 18, wherein the program instructions further cause the processor to:

in connection with the preempting, suspend execution of the second tasks of the second workload, wherein the memory pages of data are stored in the available data storage locations in the memory;

execute the first tasks of the first workload utilizing the group of resources;

retrieve the memory pages of data relating to the second workload from the memory; and based on the memory pages of data, resume the execution of the second tasks of the second workload utilizing the group of resources.

* * * * *